(12) United States Patent
Malkowski et al.

(10) Patent No.: US 9,186,136 B2
(45) Date of Patent: Nov. 17, 2015

(54) SURGICAL CLIP APPLIER

(75) Inventors: Jaroslaw T. Malkowski, Trumbull, CT (US); Kenneth Shaw, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 127 days.

(21) Appl. No.: 12/939,296

(22) Filed: Nov. 4, 2010

(65) Prior Publication Data

US 2011/0137323 A1 Jun. 9, 2011

Related U.S. Application Data

(60) Provisional application No. 61/285,006, filed on Dec. 9, 2009.

(51) Int. Cl.
| | | |
|---|---|---|
| *A61B 17/068* | (2006.01) | |
| *A61B 17/128* | (2006.01) | |
| *A61B 19/00* | (2006.01) | |

(52) U.S. Cl.
CPC .............. *A61B 17/068* (2013.01); *A61B 17/128* (2013.01); *A61B 2019/4815* (2013.01)

(58) Field of Classification Search
CPC ............ A61B 17/068; A61B 17/0682; A61B 17/0684; A61B 2019/4815
USPC .......................... 606/139, 142, 143; 227/175.1
See application file for complete search history.

(56) References Cited

U.S. PATENT DOCUMENTS

| | | | |
|---|---|---|---|
| 3,120,230 A | 2/1964 | Skold | |
| 3,638,847 A | 2/1972 | Noiles et al. | |
| 3,675,688 A * | 7/1972 | Bryan et al. | ................. 140/93 D |
| 4,242,902 A | 1/1981 | Green | |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,480,640 A | 11/1984 | Becht | |
| 4,480,641 A | 11/1984 | Failla et al. | |
| 4,487,204 A | 12/1984 | Hrouda | |
| 4,487,205 A | 12/1984 | Di Giovanni et al. | |

(Continued)

FOREIGN PATENT DOCUMENTS

| | | |
|---|---|---|
| AU | 2010200641 A1 | 10/2010 |
| CN | 100571640 C | 12/2009 |

(Continued)

OTHER PUBLICATIONS

European Search Report for EP 10252079.8-1269 date of completion is Mar. 8, 2011 (3 pages).

(Continued)

*Primary Examiner* — Alexander Orkin

(57) ABSTRACT

A surgical clip applier is provided including a housing; at least one handle pivotably connected to the housing; a channel assembly extending distally from the housing; a plurality of clips loaded in the clip carrier; a drive channel translatably supported in the housing and the channel assembly, the drive channel being translated upon actuation of the at least one handle; and a counter mechanism supported in the housing, the counter mechanism including indicia visible through the housing, wherein the indicia corresponds to a quantity of clips loaded in the clip applier, wherein the indicia decrements upon each firing of the clip applier resulting in a reduction in the quantity of clips remaining of the plurality of clips.

19 Claims, 17 Drawing Sheets

(56) References Cited

U.S. PATENT DOCUMENTS

| | | |
|---|---|---|
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon |
| 5,049,153 A | 9/1991 | Nakao et al. |
| 5,053,045 A | 10/1991 | Schmidt et al. |
| 5,059,202 A | 10/1991 | Liang et al. |
| 5,062,563 A * | 11/1991 | Green et al. ............... 227/175.3 |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen |
| 5,354,306 A | 10/1994 | Garvey, III et al. |
| 5,359,993 A * | 11/1994 | Slater et al. ................ 600/133 |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry |
| 5,382,255 A | 1/1995 | Castro |
| 5,383,881 A | 1/1995 | Green |
| 5,395,375 A | 3/1995 | Turkel et al. |
| 5,395,381 A | 3/1995 | Green |
| 5,403,327 A | 4/1995 | Thornton et al. |
| 5,409,498 A | 4/1995 | Braddock et al. |
| 5,413,584 A | 5/1995 | Scjulze |
| 5,423,835 A | 6/1995 | Green |
| 5,425,740 A | 6/1995 | Hutchinson, Jr. |
| 5,431,667 A | 7/1995 | Thompson |
| 5,431,668 A | 7/1995 | Burbank, III et al. |
| 5,431,669 A | 7/1995 | Thompson |
| 5,439,468 A | 8/1995 | Schulze et al. |
| 5,441,509 A | 8/1995 | Vidal |
| 5,447,513 A | 9/1995 | Davison et al. |
| 5,449,365 A | 9/1995 | Green |
| 5,462,555 A | 10/1995 | Bolanos |
| 5,462,558 A | 10/1995 | Kolesa |
| 5,464,416 A | 11/1995 | Steckel |

(56) References Cited

U.S. PATENT DOCUMENTS

| | | |
|---|---|---|
| 5,474,566 A | 12/1995 | Alesi |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips |
| 5,514,149 A | 5/1996 | Green |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green |
| 5,527,320 A | 6/1996 | Carruthers et al. |
| 5,542,949 A | 8/1996 | Yoon |
| 5,547,474 A | 8/1996 | Kloeckl |
| 5,569,274 A | 10/1996 | Rapacki et al. |
| 5,571,121 A | 11/1996 | Heifetz |
| 5,575,802 A | 11/1996 | McQuildin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt |
| 5,618,291 A | 4/1997 | Thompson |
| 5,618,306 A | 4/1997 | Roth et al. |
| 5,620,452 A | 4/1997 | Yoon |
| 5,626,585 A | 5/1997 | Mittelstadt |
| 5,626,586 A | 5/1997 | Pistl et al. |
| 5,626,587 A | 5/1997 | Bishop et al. |
| 5,626,592 A | 5/1997 | Phillips |
| RE35,525 E | 6/1997 | Stefanchik et al. |
| 5,634,930 A | 6/1997 | Thornton et al. |
| 5,643,291 A | 7/1997 | Pier |
| 5,645,551 A | 7/1997 | Green |
| 5,645,553 A | 7/1997 | Kolesa |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier |
| 5,695,505 A | 12/1997 | Yoon |
| 5,697,938 A | 12/1997 | Jensen et al. |
| 5,700,270 A | 12/1997 | Peyser |
| 5,700,271 A | 12/1997 | Whitfield |
| 5,702,048 A | 12/1997 | Eberlin |
| 5,709,706 A | 1/1998 | Kienzle et al. |
| 5,713,911 A | 2/1998 | Racenet |
| 5,713,912 A | 2/1998 | Porter |
| 5,720,756 A | 2/1998 | Green |
| 5,722,982 A | 3/1998 | Ferreira et al. |
| 5,725,537 A | 3/1998 | Green |
| 5,725,538 A | 3/1998 | Green |
| 5,725,542 A | 3/1998 | Yoon |
| 5,733,295 A | 3/1998 | Back et al. |
| 5,755,726 A | 5/1998 | Pratt |
| 5,766,189 A | 6/1998 | Matsuno |
| 5,769,857 A | 6/1998 | Reztzov et al. |
| 5,772,673 A | 6/1998 | Cuny |
| 5,776,146 A | 7/1998 | Sackier et al. |
| 5,776,147 A | 7/1998 | Dolendo |
| 5,779,718 A | 7/1998 | Green |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts |
| 5,792,150 A | 8/1998 | Pratt |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield |
| 5,833,700 A | 11/1998 | Fogelberg et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser |
| 5,868,761 A | 2/1999 | Nicholas |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser |
| 5,951,574 A | 9/1999 | Stefanchik et al. |
| 5,972,003 A | 10/1999 | Rousseau |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,045,560 A | 4/2000 | McKean et al. |
| RE36,720 E | 5/2000 | Green |
| 6,059,799 A | 5/2000 | Aranyi |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis |
| 6,537,289 B1 | 3/2003 | Kayan |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan |
| 6,676,659 B2 | 1/2004 | Hutchins et al. |
| 6,679,894 B2 | 1/2004 | Damarati |
| RE38,445 E | 2/2004 | Pistl |
| 6,695,854 B1 | 2/2004 | Kayan |
| 6,706,057 B1 | 3/2004 | Bidoia et al. |
| 6,716,226 B2 | 4/2004 | Sixto, Jr. et al. |

(56) References Cited

U.S. PATENT DOCUMENTS

| | | |
|---|---|---|
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,637,917 B2 | 12/2009 | Whitfield |
| 7,695,482 B2 | 4/2010 | Viola |
| 7,717,926 B2 | 5/2010 | Whitfield |
| 7,727,248 B2 | 6/2010 | Smith et al. |
| 7,819,886 B2 | 10/2010 | Whitfield |
| 7,887,553 B2 | 2/2011 | Lehman et al. |
| 7,905,890 B2 | 3/2011 | Whitfield |
| 7,942,885 B2 | 5/2011 | Sixto, Jr. et al. |
| 7,963,433 B2 | 6/2011 | Whitman et al. |
| 7,988,027 B2 | 8/2011 | Olson |
| 8,011,550 B2 | 9/2011 | Aranyi |
| 8,011,555 B2 | 9/2011 | Tarinelli |
| 8,016,178 B2 | 9/2011 | Olson |
| 8,021,375 B2 | 9/2011 | Aldrich |
| 8,021,378 B2 | 9/2011 | Sixto, Jr. |
| 8,056,565 B2 | 11/2011 | Zergiebel |
| 8,062,310 B2 | 11/2011 | Shibata et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,080,021 B2 | 12/2011 | Griego |
| 8,083,668 B2 | 12/2011 | Durgin |
| 8,088,061 B2 | 1/2012 | Wells |
| 8,091,755 B2 | 1/2012 | Kayan |
| 8,100,926 B1 | 1/2012 | Filshie et al. |
| 8,128,643 B2 | 3/2012 | Aranyi |
| 8,142,451 B2 | 3/2012 | Boulnois |
| 8,157,149 B2 | 4/2012 | Olson |
| 8,157,151 B2 | 4/2012 | Ingmanson |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema |
| 8,236,012 B2 | 8/2012 | Molitor |
| 8,246,634 B2 | 8/2012 | Huitema |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,282,655 B2 | 10/2012 | Whitfield |
| 8,308,743 B2 | 11/2012 | Matsuno et al. |
| 8,328,822 B2 | 12/2012 | Huitema |
| 8,336,556 B2 | 12/2012 | Zergiebel |
| 8,348,130 B2 | 1/2013 | Shah |
| 8,357,171 B2 | 1/2013 | Whitfield |
| 8,366,726 B2 | 2/2013 | Dennis |
| 8,371,491 B2 | 2/2013 | Huitema |
| 8,372,095 B2 | 2/2013 | Viola |
| 8,382,773 B2 | 2/2013 | Whitfield |
| 8,398,655 B2 | 3/2013 | Cheng et al. |
| 8,403,945 B2 | 3/2013 | Whitfield |
| 8,403,946 B2 | 3/2013 | Whitfield |
| 8,409,222 B2 | 4/2013 | Whitfield |
| 8,409,223 B2 | 4/2013 | Sorrentino |
| 8,419,752 B2 | 4/2013 | Sorrentino |
| 8,430,892 B2 | 4/2013 | Bindra |
| 8,444,660 B2 | 5/2013 | Adams |
| 8,465,502 B2 | 6/2013 | Zergiebel |

(56) References Cited

U.S. PATENT DOCUMENTS

| | | |
|---|---|---|
| 8,475,473 B2 | 7/2013 | Vandenbroek |
| 8,480,688 B2 | 7/2013 | Boulnois |
| 8,486,091 B2 | 7/2013 | Sorrentino |
| 8,491,608 B2 | 7/2013 | Sorrentino |
| 8,496,673 B2 | 7/2013 | Nguyen |
| 8,506,580 B2 | 8/2013 | Zergiebel |
| 8,512,357 B2 | 8/2013 | Viola |
| 8,523,882 B2 | 9/2013 | Huitema |
| 8,529,585 B2 | 9/2013 | Jacobs |
| 8,529,586 B2 | 9/2013 | Rosenberg |
| 8,529,588 B2 | 9/2013 | Ahlberg |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield |
| 8,585,717 B2 | 11/2013 | Sorrentino |
| 8,603,109 B2 | 12/2013 | Aranyi |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,709,027 B2 | 4/2014 | Adams et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,920,438 B2 | 12/2014 | Aranyi et al. |
| 8,961,542 B2 | 2/2015 | Whitfield et al. |
| 8,968,337 B2 | 3/2015 | Whitfield et al. |
| 8,973,804 B2 | 3/2015 | Hess et al. |
| 9,011,464 B2 | 4/2015 | Zammataro |
| 9,011,465 B2 | 4/2015 | Whitfield et al. |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0208231 A1 | 11/2003 | Williamson, IV et al. |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2004/0167545 A1* | 8/2004 | Sadler et al. .................. 606/142 |
| 2004/0193213 A1 | 9/2004 | Aranyi |
| 2005/0070925 A1* | 3/2005 | Shelton et al. ................ 606/142 |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |

(56) References Cited

U.S. PATENT DOCUMENTS

| | | |
|---|---|---|
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santili et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0243145 A1 | 10/2008 | Whitfield et al. |
| 2009/0045242 A1* | 2/2009 | Viola ......................... 227/177.1 |
| 2010/0057105 A1 | 3/2010 | Sorrentino |
| 2010/0057107 A1 | 3/2010 | Sorrentino |
| 2010/0274262 A1 | 10/2010 | Schulz et al. |
| 2010/0274264 A1 | 10/2010 | Schulz et al. |
| 2011/0087242 A1 | 4/2011 | Pribanic |
| 2011/0137323 A1 | 6/2011 | Malkowski |
| 2011/0208212 A1 | 8/2011 | Zergiebel |
| 2011/0224701 A1 | 9/2011 | Menn |
| 2011/0245847 A1 | 10/2011 | Menn |
| 2012/0029534 A1 | 2/2012 | Whitfield |
| 2012/0109158 A1 | 5/2012 | Zammataro |
| 2012/0116420 A1 | 5/2012 | Sorrentino |
| 2012/0123446 A1 | 5/2012 | Aranyi |
| 2012/0197269 A1 | 8/2012 | Zammataro |
| 2012/0265220 A1 | 10/2012 | Menn |
| 2012/0277765 A1 | 11/2012 | Zammataro |
| 2012/0330326 A1 | 12/2012 | Creston |
| 2013/0110135 A1 | 5/2013 | Whitfield |
| 2013/0131697 A1 | 5/2013 | Hartoumbekis |
| 2013/0165951 A1 | 6/2013 | Blake, III |
| 2013/0165952 A1 | 6/2013 | Whitfield |
| 2013/0172910 A1 | 7/2013 | Malkowski |
| 2013/0172911 A1 | 7/2013 | Rockrohr |
| 2013/0172912 A1 | 7/2013 | Whitfield |
| 2013/0190779 A1 | 7/2013 | Whitfield |
| 2013/0190780 A1 | 7/2013 | Whitfield |
| 2013/0253541 A1 | 9/2013 | Zergiebel |
| 2013/0274767 A1 | 10/2013 | Sorrentino |
| 2013/0289583 A1 | 10/2013 | Zergiebel |
| 2013/0296891 A1 | 11/2013 | Hartoumbekis |
| 2013/0296892 A1 | 11/2013 | Sorrentino |
| 2013/0310849 A1 | 11/2013 | Malkowski |
| 2013/0325040 A1 | 12/2013 | Zammataro |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0194903 A1 | 7/2014 | Malkowski et al. |
| 2014/0207156 A1 | 7/2014 | Malkowski |
| 2014/0316441 A1 | 10/2014 | Zergiebel et al. |
| 2014/0330291 A1 | 11/2014 | Whitfield et al. |
| 2015/0005790 A1 | 1/2015 | Whitfield et al. |
| 2015/0032131 A1 | 1/2015 | Sorrentino et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |

FOREIGN PATENT DOCUMENTS

| | | |
|---|---|---|
| CN | 101664329 A | 3/2010 |
| DE | 20 2009 006 113 | 7/2009 |
| EP | 0 086 721 | 8/1983 |
| EP | 0085931 A2 | 8/1983 |
| EP | 0 089 737 A1 | 9/1983 |
| EP | 0324166 A2 | 7/1989 |
| EP | 0392750 A1 | 10/1990 |
| EP | 0 409 569 A1 | 1/1991 |
| EP | 0 569 223 | 11/1993 |
| EP | 0 594 003 | 4/1994 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 | 4/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 187 | 10/2006 |
| EP | 1 712 191 A2 | 10/2006 |
| EP | 1 757 236 | 2/2007 |
| EP | 1 813 199 A1 | 8/2007 |
| EP | 1 894 531 A2 | 3/2008 |
| EP | 1 908 423 | 4/2008 |
| EP | 1 908 423 A2 | 4/2008 |
| EP | 1 913 881 A1 | 4/2008 |
| EP | 1 939 231 A1 | 7/2008 |
| EP | 2 229 895 A1 | 9/2010 |
| EP | 2 332 471 | 6/2011 |
| EP | 2 412 318 A2 | 2/2012 |
| GB | 2073022 A | 10/1981 |
| JP | 10-118083 A | 5/1998 |
| JP | 2003 033361 A | 2/2003 |
| JP | 2006-501954 A | 1/2006 |
| JP | 2006-154230 A | 6/2006 |
| JP | 2006-209948 A | 8/2006 |
| JP | 2006-277221 A | 10/2006 |
| JP | 2007-250843 A | 9/2007 |
| JP | 2008-017876 A | 1/2008 |
| JP | 2008-047498 A | 2/2008 |
| JP | 2008-055165 A | 3/2008 |
| JP | 2008-515550 A | 5/2008 |
| JP | 2009-198991 A | 9/2009 |
| JP | 54-99386 B2 | 5/2014 |

(56) References Cited

FOREIGN PATENT DOCUMENTS

| | | |
|---|---|---|
| WO | WO 01/66001 | 9/2001 |
| WO | WO 01/67965 | 9/2001 |
| WO | WO 03/086207 | 10/2003 |
| WO | WO 03/092473 | 11/2003 |
| WO | 2004-032762 A1 | 4/2004 |
| WO | WO 2005/091457 A1 | 9/2005 |
| WO | WO 2006/042076 | 4/2006 |
| WO | WO 2006/042076 A2 | 4/2006 |
| WO | WO 2006/042084 A2 | 4/2006 |
| WO | WO 2006/042110 | 4/2006 |
| WO | WO 2006/042110 A2 | 4/2006 |
| WO | WO 2006/042141 | 4/2006 |
| WO | WO 2006/135479 | 12/2006 |
| WO | WO 2008/118928 | 10/2008 |
| WO | WO 2008/118928 A2 | 10/2008 |
| WO | WO 2008/127968 | 10/2008 |
| WO | WO 2008/127968 A2 | 10/2008 |

OTHER PUBLICATIONS

Extended European Search Report corresponding to European Application No. EP 11250214.1, completed May 25, 2011; mailed Jun. 1, 2011; (3 Pages).
European Search Report corresponding to EP 05810218.7, mailed on May 20, 2011; completed on Apr. 18, 2011; 3 pages.
European Search Report corresponding to EP 05807612.6, mailed on May 20, 2011; completed on May 2, 2011; 3 pages.
Extended European Search Report corresponding to EP 10251737.2, mailed on May 20, 2011; completed on May 9, 2011; 4 pages.
Extended International Search Report corresponding to European Application No. 07 25 3905.9, completed Jan. 29, 2008: mailed Feb. 7, 2008; (7 Pages).
Partial International Search Report corresponding to European Application No. EP 07 25 3807.7, completed Jul. 23. 2008; mailed Aug. 1, 2008; (3 pages).
International Search Report corresponding to International Application No. PCT/US08/58185, completed Sep. 4. 2008; mailed Sep. 9, 2008: (2 Pages).
International Search Report corresponding to International Application No. PCT/US08/59859, completed Sep. 14. 2008; mailed Sep. 18, 2008; (2 Pages).
Extended European Search Report corresponding to European Application No. EP 07 25 3807.7, completed Nov. 7, 2008; mailed Nov. 26, 2008; (11 Pages).
Extended European Search Report corresponding to European Application No. EP 09252049.3, completed Dec. 11, 2009; mailed Jan. 12, 2010; (3 Pages).
Extended European Search Report corresponding to European Application No. EP 09252050.1, completed Dec. 23, 2009; mailed Jan. 21, 2010; (3 Pages).
Extended European Search Report corresponding to European Application No. EP 09252051.9, completed Dec. 21, 2009; mailed Jan. 28, 2010; (3 Pages).
Extended European Search Report corresponding to European Application No. EP 09252052.7, completed Nov. 16, 2009; mailed Nov. 24, 2009; (3 Pages).
Extended European Search Report corresponding to European Application No. EP 09252053.5, completed Nov. 24, 2009; mailed Dec. 1, 2009; (3 Pages).
Extended European Search Report corresponding to European Application No. EP 09252054.3. completed Jan. 7, 2010; mailed Jan. 22, 2010; (3 Pages).
Extended European Search Report corresponding to European Application No. EP 09252056.8, completed Jan. 8, 2010; mailed Feb. 5, 2010; (3 Pages).
Extended European Search Report corresponding to European Application No. 10250497.4, completed May 4, 2010; mailed May 12, 2010; (6 Pages).

"Salute II Disposable Fixation Device", Technique Guide—Laparoscopic and Open Inguinal and Ventral Hernia Repair; Davol, A Bard Company, 2006; (7 Pages).
European Search Report corresponding to European Application No. EP 05 80 2686.5, completed Jan. 9, 2012; mailed Jan. 18, 2012; (3 Pages).
Extended European Search Report corresponding to European Application No. EP 12 15 1313.9, completed Mar. 20, 2012 and mailed Apr. 12, 2012; (5 Pages).
European Search Report for corresponding EP12161291 date of mailing is May 4, 2012 (5 pgs).
Extended European Search Report corresponding to European Application No. EP 12 16 2288.0, completed Jun. 4, 2012 and mailed Jul. 7, 2012; (6 Pages).
Extended European Search Report corresponding to European Application No. EP 12 16 5891.8, completed Jun. 12, 2012 and mailed Jun. 20, 2012; (6 Pages).
Extended European Search Report corresponding to European Application No. EP 12 16 4955.2, completed Aug. 23, 2012 and mailed Sep. 4, 2012; (5 Pages).
Extended European Search Report corresponding to European Application No. EP 12 18 6401.1, completed Nov. 22, 2012 and mailed Nov. 30, 2012; (7 Pages).
Extended European Search Report corresponding to European Application No. EP 12 18 6448.2, completed Nov. 28, 2012 and mailed Dec. 10, 2012; (6 Pages).
Extended European Search Report corresponding to European Application No. EP 12 19 1706.6, completed Dec. 19, 2012 and mailed Jan. 8, 2013; (6 Pages).
Extended European Search Report corresponding to European Application No. EP 11 25 0754.6, completed Oct. 22, 2012 and mailed Oct. 31, 2012; (6 Pages).
Extended European Search Report corresponding to EP 13 16 6382.5, completed Nov. 19, 2013 and mailed Nov. 28, 2013; (8 pp).
Extended European Search Report corresponding to EP 11 25 0194.5, completed Nov. 25, 2013 and mailed Dec. 3, 2013; (8 pp).
Extended European Search Report corresponding to EP 10 25 1798.4, completed Dec. 12, 2013 and mailed Jan. 2, 2014; (9 pp).
Extended European Search Report corresponding to EP 12 19 8745.7, completed Mar. 19, 2013 and mailed Apr. 11, 2013; (8 pp).
Extended European Search Report corresponding to EP 12 15 2989.5, completed Apr. 9, 2013 and mailed Apr. 18, 2013; (9 pp).
Extended European Search Report corresponding to EP 08 73 2820.9, completed Jul. 2, 2013 and mailed Jul. 9, 2013; (10 pp).
Extended European Search Report corresponding to EP 12 19 1706.6, completed Dec. 19, 2012 and mailed Jan. 8, 2013; (6 pp).
Extended European Search Report corresponding to EP 13 17 2008.8, completed Aug. 14, 2013 and mailed Aug. 28, 2013; (8 pp).
Extended European Search Report corresponding to EP 10 25 2112.7, completed Jul. 29, 2014 and mailed Aug. 5, 2014; (8 pp).
Extended European Search Report corresponding to EP 14 15 1673.2, completed Apr. 25, 2014 and mailed May 8, 2014; (8 pp).
Japanese Office Action corresponding to JP 2011-160130 mailed Dec. 1, 2014.
Chinese Office Action corresponding to CN 201210015011.8 issued Jan. 4, 2015.
Japanese Office Action corresponding to JP 2011-160126 mailed Jan. 9, 2015.
Japanese Office Action corresponding to JP 2011-184521 mailed Jan. 15, 2015.
Extended European Search Report corresponding to 14 18 2236.1 dated Jan. 20, 2015.
Chinese Office Action corresponding to CN 201110201736.1 issued Feb. 9, 2015.
Extended European Search Report corresponding to EP 14 16 1540.1 dated Feb. 27, 2015.
Australian Office Action corresponding to AU 2010226985 issued Mar. 31, 2015.
Australian Office Action corresponding to AU 2013211526 issued Apr. 6, 2015.
Australian Office Action corresponding to AU 2011211463 issued Apr. 13, 2015.

(56) References Cited

OTHER PUBLICATIONS

Australian Office Action corresponding to AU 2013254887 issued Apr. 14, 2015.
Japanese Office Action corresponding to JP 2013-225272 mailed May 1, 2015.
European Office Action corresponding to EP 12 152 989.5 dated May 4, 2015.
Australian Office Action corresponding to AU 2009212759 issued May 7, 2015.
Japanese Office Action corresponding to JP 2013-229070 mailed May 8, 2015.
Japanese Office Action corresponding to JP 2013-229996 mailed May 8, 2015.
Japanese Office Action corresponding to JP 2014-190735 dated May 27, 2015; no English translation attached—unavailable.

* cited by examiner

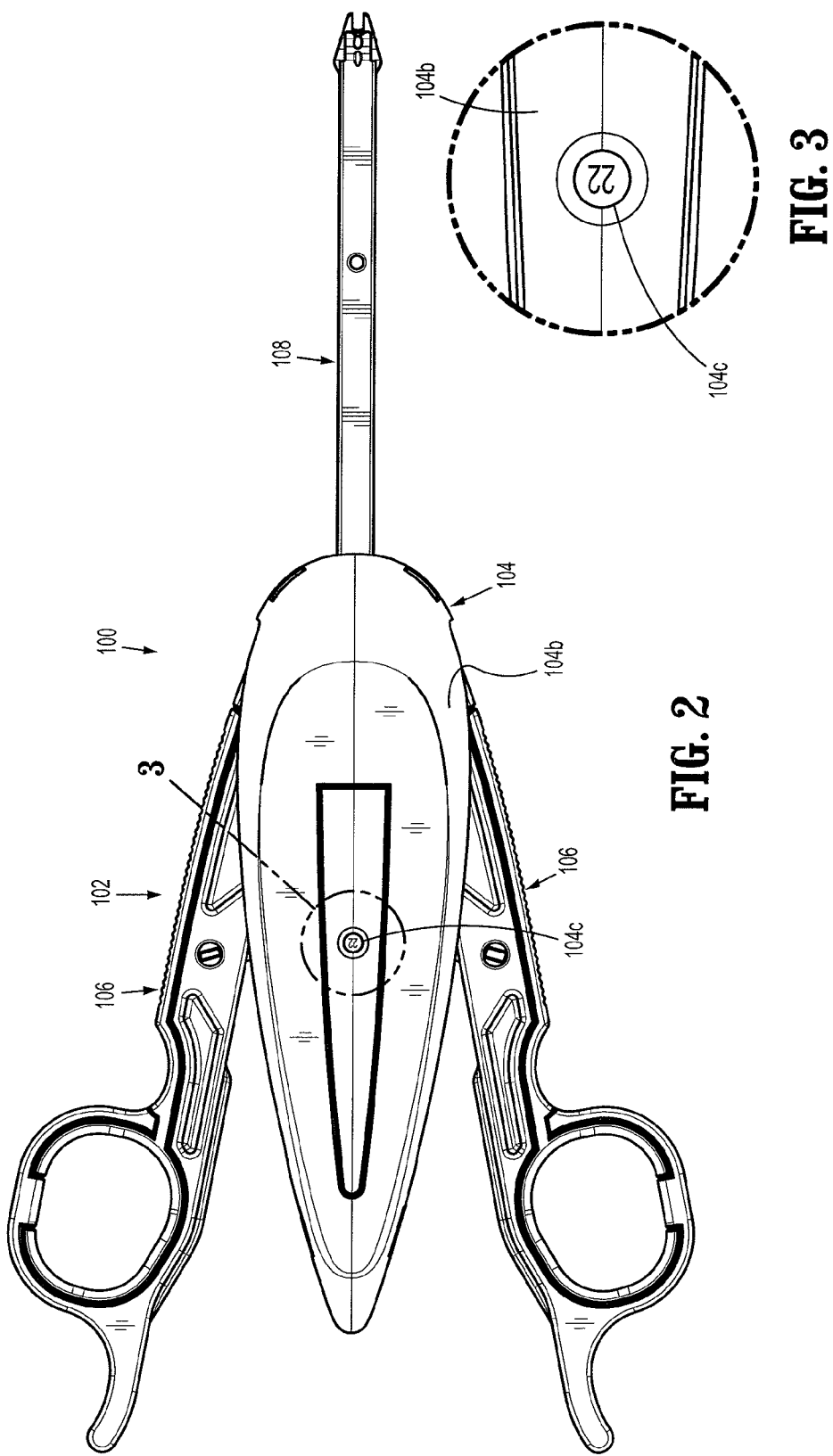

SURGICAL CLIP APPLIER

CROSS REFERENCE TO RELATED APPLICATION

The present application claims the benefit of and priority to U.S. Provisional Application Ser. No. 61/285,006, filed on Dec. 9, 2009, the entire content of which is incorporate herein by reference.

BACKGROUND

1. Technical Field

The present application relates to surgical instruments, and more particularly, to surgical clip appliers having a plurality of clips for applying the clips to body tissues and vessels during surgical procedures.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank, III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

A need exists for a user of the clip applier to know how many clips remain in the clip applier and/or to know when a final clip of the plurality of clips has been fired.

SUMMARY

The present application relates to surgical clip appliers having a plurality of clips for applying the clips to body tissues and vessels during surgical procedures and their methods of use.

According to an aspect of the present disclosure, a surgical clip applier is provided including a housing; at least one handle pivotably connected to the housing; a channel assembly extending distally from the housing; a plurality of clips loaded in the clip carrier; a drive channel translatably supported in the housing and the channel assembly, the drive channel being translated upon actuation of the at least one handle; and a counter mechanism supported in the housing, the counter mechanism including indicia visible through the housing, wherein the indicia corresponds to a quantity of clips loaded in the clip applier, wherein the indicia decrements upon each firing of the clip applier resulting in a reduction in the quantity of clips remaining of the plurality of clips.

The counter mechanism may be rotatably supported in the housing and may include a uni-directional clutch member permitting rotation of the counter mechanism in a single direction. The counter mechanism may include a counter dial rotatably supported in the housing, wherein the counter dial includes the indicia thereof; and a counter clutch operatively connected to the counter dial such that rotation of the counter clutch in a first direction results in rotation of the counter dial in the first direction, and rotation of the counter clutch in second direction results in no rotation of the counter dial.

The counter mechanism may include a latch member operatively engaged with the counter dial. In use, the latch member permits rotation of the counter dial in the first direction and inhibits rotation of the counter mechanism in a direction opposite to the first direction.

The counter dial may include a plurality of grooves formed in an outer periphery thereof, and the latch member may include a resilient finger biased into engagement with the plurality of grooves of the counter dial.

The counter clutch may be concentrically, rotatably nested in a bore defined in the counter dial. The counter clutch may include at least one resilient finger extending therefrom for engagement with uni-directional teeth formed in a perimetrical surface of the bore of the counter dial.

The drive channel may define an angled slot therein, and the counter clutch may include a clutch pin extending from a surface thereof and may be slidably disposed in the angled slot of the drive channel. In use, translation of the drive channel in a first direction relative to the counter mechanism would cause the clutch pin to be cammed by the angled slot thereof thereby causing the counter clutch to rotate in the first direction, and translation of the drive channel in a second direction relative to the counter mechanism would cause the clutch pin to be cammed by the angled slot thereof thereby causing the counter clutch to rotate in the second direction.

The counter mechanism may include a latch member operatively engaged with the counter dial. In use, the latch member permits rotation of the counter dial in the first direction and inhibits rotation of the counter mechanism in a direction opposite to the first direction.

The counter mechanism may include a counter dial defining a lock out groove formed in an outer perimetrical edge thereof; and a lock out supported in the housing. The lock out may be biased such that a first catch thereof engages against the outer perimetrical edge of the counter dial. In use, as the counter dial is rotated and the lock out groove of the counter dial is brought into registration with the first catch of the lock out, the first catch of the lock out is urged into the lock out groove thereby preventing a rotation of the counter dial in an opposite direction.

The lock out may include a second catch. In use, the second catch of the lock out moves into a path of a translating member of the clip applier when the first catch of the lock out is moved into the lock out groove of the counter dial, thereby inhibiting a translation of the translating member of the clip applier.

The lock out groove of the counter dial may move into registration with the first catch of the lock out when a final clip of the plurality of clips has been fired. The lock out groove of the counter dial may be associated with an indicia on the counter mechanism indicating that the final clip has been fired. The indicia on the counter mechanism, indicating that the final clip of the plurality of clip has been fired, may be represented by the number "zero."

The clip applier may further include a ratchet mechanism having a ratchet pawl pivotably supported in the housing; and a rack member provided on the translating member. The rack member may be in operative registration with the ratchet pawl. In use, the rack member translates across the ratchet pawl as the translating member translates. The ratchet mechanism may be prevented from re-setting when the rack member has not completed a fully translation.

BRIEF DESCRIPTION OF THE DRAWINGS

The present clip applier will be more fully appreciated as the same becomes better understood from the following detailed description when considered in connection with the following drawings, in which:

FIG. 2 is a top, plan view of the surgical clip applier of FIG. 1;

FIG. 3 is an enlarged view of the indicated area of detail of FIG. 2;

DETAILED DESCRIPTION OF EMBODIMENTS

Figure 1:
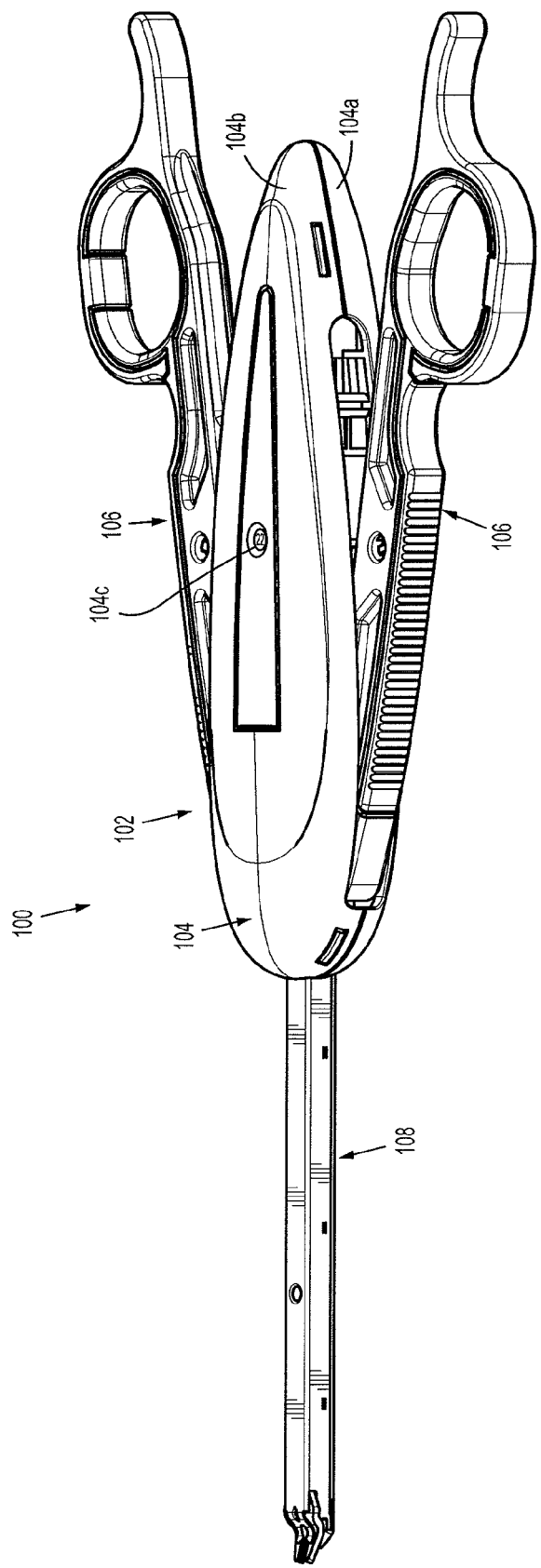
FIG. 1 is a perspective view of a surgical clip applier according to an embodiment of the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-5, a surgical clip applier in accordance with an embodiment of the present disclosure is generally designated as 100. Surgical clip applier 100 generally includes a handle assembly 102 including a housing 104 having an upper housing half 104a and lower housing half 104b. Handle assembly 102 further includes a pair of handles 106 pivotably secured to housing 104 and extending outwardly therefrom. A channel assembly 108 is fixedly secured to housing 104 and extends outwardly therefrom, terminating in a jaw assembly 110.

As seen in FIGS. 1-5, housing halves 104a and 104b of clip applier 100 fit together by snap fit engagement with one another. Housing 104 defines a window 104c formed in lower housing half 104b for supporting and displaying a counter mechanism, as will be discussed in greater detail below.

Figure 4:
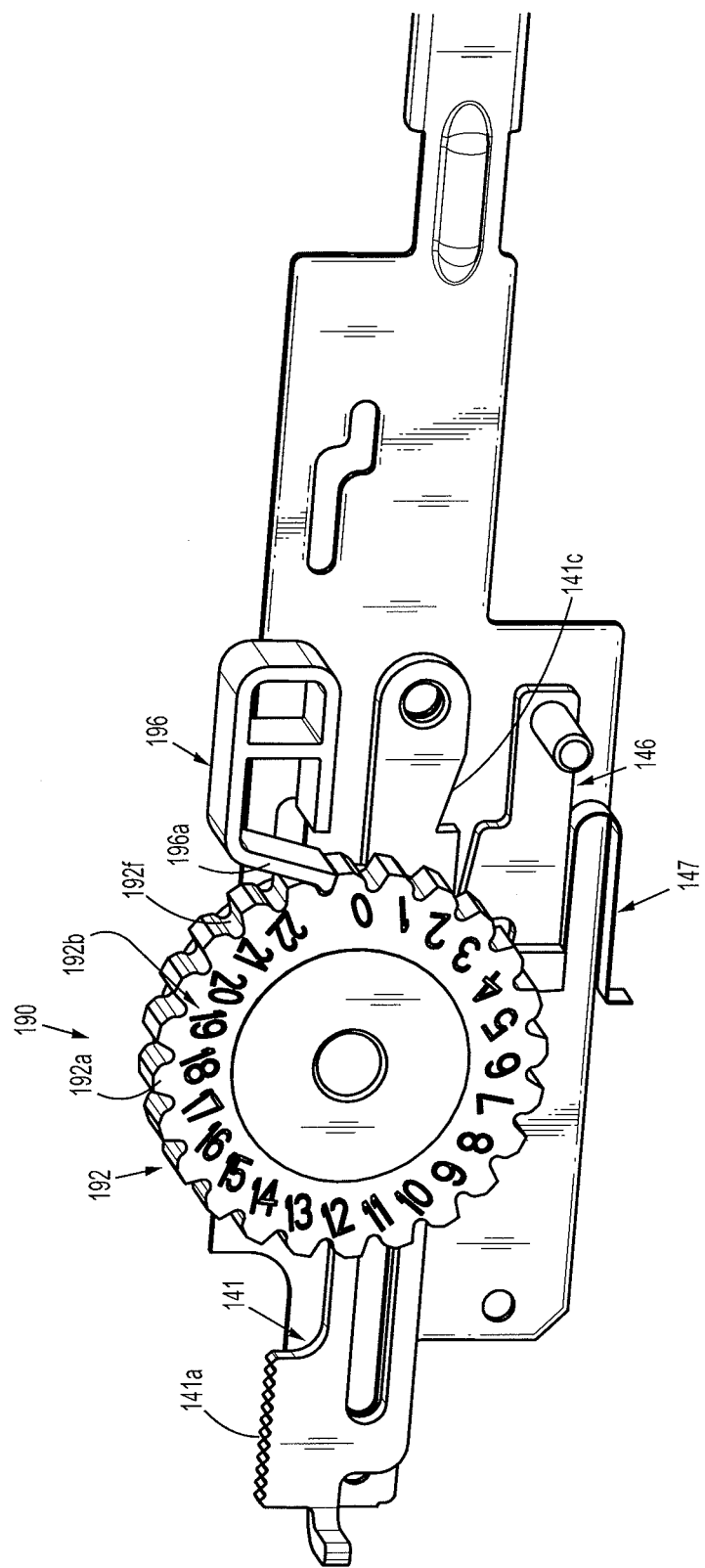
FIG. 4 is a perspective view of a mechanical counter assembly of the surgical clip applier of FIGS. 1 and 2.

As seen in FIG. 4, handles 106 are secured to housing 104 by handle pivot posts 104d extending from lower housing half 104b and into respective apertures 106a formed in handles 106. Handle assembly 102 includes a link member 122 pivotally connected to each handle 106 at a pivot point 106b formed in a respective handle 106. A distal end of each link member 122 is pivotally connected to a pivot point formed in a drive channel 140 via a drive pin 124. Each end of drive pin 124 is slidably received in an elongate channel formed in a respective upper and lower housing half 104a, 104b. In use, as will be described in greater detail below, as handles 106 are squeezed, link members 122 push drive channel 140 distally via drive pin 124.

Channel assembly 108 includes a channel or cartridge cover 130 and an outer or lower channel 132 each having a proximal end retained in housing assembly 102, between upper and lower housing halves 104a, 104b.

Figure 5:
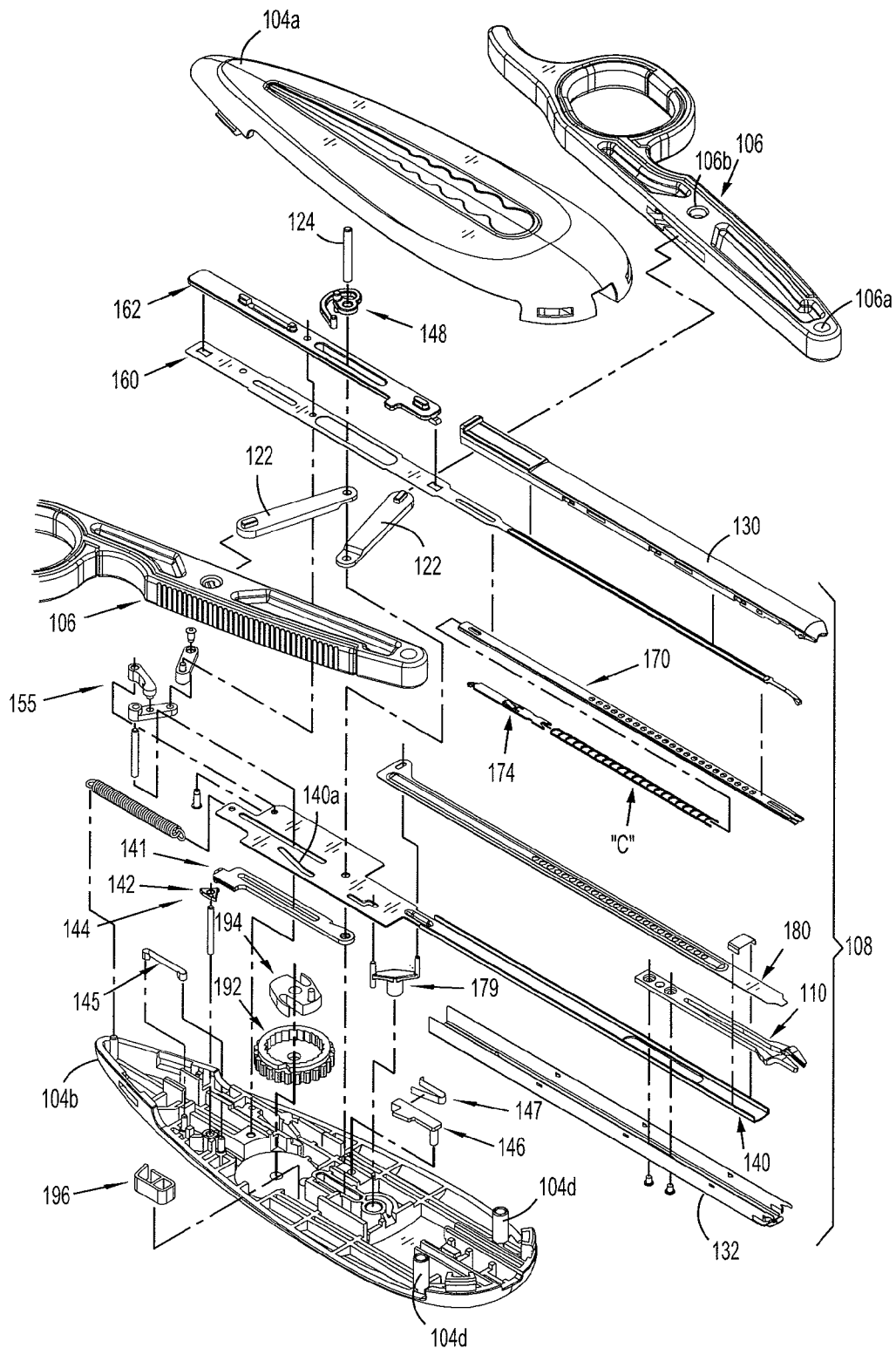
FIG. 5 is an exploded perspective view of the surgical clip applier of FIGS. 1-4.

As seen in FIG. 5, clip applier 100 includes a clip pusher bar 160 slidably disposed beneath cartridge cover 130, a stabilizer 162 configured to overlie and engage pusher bar 160, a motion multiplier system 155 supported in housing 104, a clip carrier 170 disposed within channel assembly 108 and beneath pusher bar 160, a stack of surgical clips "C" loaded and/or retained within clip carrier 170 in a manner so as to slide therewithin and/or therealong, a clip follower 174 slidably disposed within clip carrier 170 and positioned behind the stack of surgical clips "C," a wedge plate 180 slidably disposed within handle assembly 102 and channel assembly 108, a wedge plate pivot arm 179 pivotally supported in lower housing half 104b of housing 104 for transmitting translation of drive channel 140 to translation of wedge plate 180, a drive channel 140 reciprocally supported in and extending between housing 104 of handle assembly 102 and channel assembly 108, an audible/tactile indicator 148 connected to drive channel 140 via drive pin 124, and a jaw assembly 110 mounted on or at a distal end of channel assembly 108 and actuatable by handles 106 of handle assembly 102.

Reference may be made to U.S. Provisional Application No. 61/091,467, filed on Aug. 25, 2008, entitled "Surgical Clip Applier" and U.S. Provisional Application No. 61/091, 485, filed on Aug. 25, 2008, entitled "Surgical Clip Applier and Method of Assembly," the entire contents of each of which being incorporated herein by reference, for a detailed discussion of the structure, operation, and method of assembly of various components surgical clip applier 100. Reference may also be made to U.S. Provisional Application No. 61/286,569, filed on Dec. 15, 2009, entitled "Surgical Clip Applier", the entire contents of which is incorporated herein by reference, for additional detailed discussion of the structure, operation, and method of assembly of various components of surgical clip applier 100.

As seen in FIGS. 1-12, clip applier 100 further includes a mechanical counter mechanism 190 supported in housing 104 of handle assembly 102. Counter mechanism 190 includes a counter dial 192 rotatably disposed within housing 104 so as to overlie window 104c formed in lower housing half 104b, a counter clutch 194 operatively connected to counter dial 192 and configured to permit uni-directional rotation of counter dial 192, and a latch member 196 configured to engage counter dial 192.

As seen in FIGS. 4-11, counter dial 192 includes a first face 192a disposed adjacent window 104c formed in lower housing half 104b. First face 192a includes a plurality of indicia 192b, in the form of sequential numbers disposed thereof and substantially around a radial periphery thereof. Indicia 192b may correspond to the number of clips that are loaded in clip applier 100. By way of example only, indicia 192b may be numerals from "0-22." Indicia 192b are located on first face 192a so as to be in registration with window 104c formed in lower housing half 104b. Counter dial 192 includes a second face 192c, opposite first face 192b, and defining a bore 192d therein. Bore 192d includes a radial array of uni-directional teeth 192e formed therein. Counter dial 192 further includes a first or outer rim defining a plurality of grooves 192f formed around an outer periphery thereof, and a second or inner rim defining a single groove 192g formed in an outer periphery thereof.

With continued reference to FIGS. 4-11, counter clutch 194 is concentrically and rotatably nested in bore 192d of counter dial 192. Counter clutch 194 of mechanical counter mechanism 190 includes a body portion 194a configured and dimensioned for rotatable disposition in bore 192d of counter dial 192. Counter clutch 194 includes a pair of opposed resilient fingers 194b, 194c extending substantially tangentially from body portion 194a. Resilient fingers 194b, 194c extend from body portion 194a by an amount sufficient so as to resiliently engage uni-directional teeth 192e of dial 192. Counter clutch 194 includes a clutch pin 194d extending from body portion 194a and projecting out of bore 192d of counter dial 192.

As seen in FIGS. 4-9, latch member 196 of mechanical counter mechanism 190 is secured to lower housing half 104b. Latch member 196 includes a resilient finger 196a configured to contact and selectively engage grooves 192f formed around the outer periphery of counter dial 192.

Figure 6:
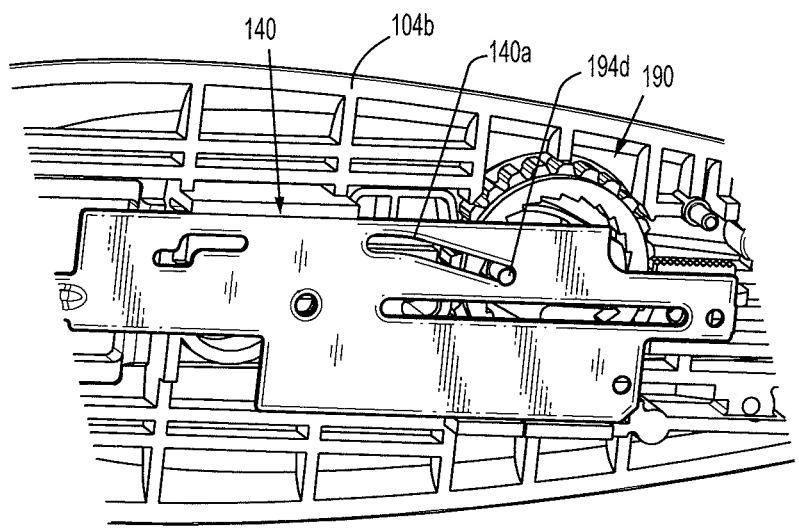
FIG. 6 is a perspective view of a handle assembly with a housing half-section removed therefrom and illustrating a counter of the mechanical counter assembly engaged with a drive channel.
Figure 7:
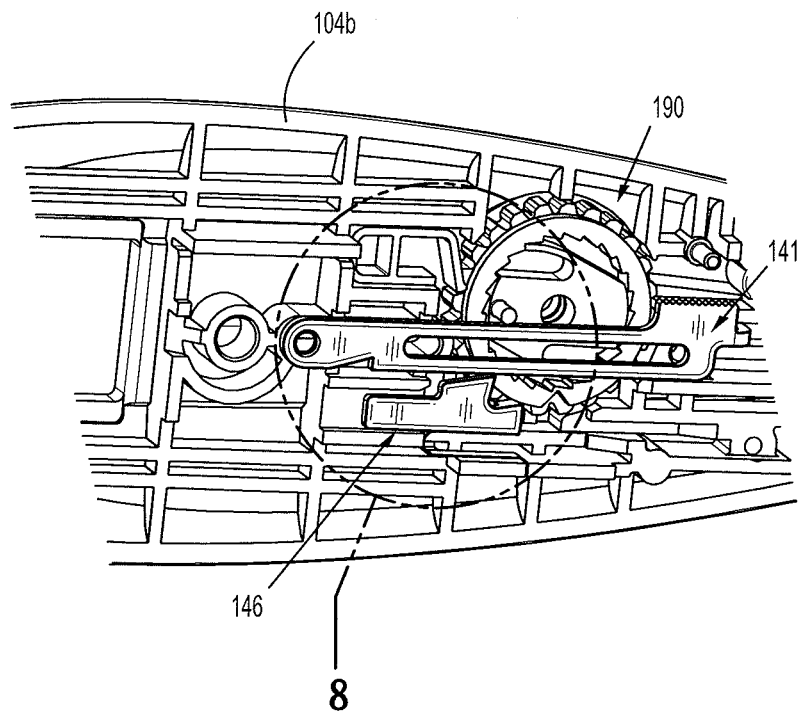
FIG. 7 is a perspective view of a handle assembly with a housing half-section and drive channel removed therefrom and illustrating the counter of the mechanical counter assembly engaged with a ratchet.
Figure 8:
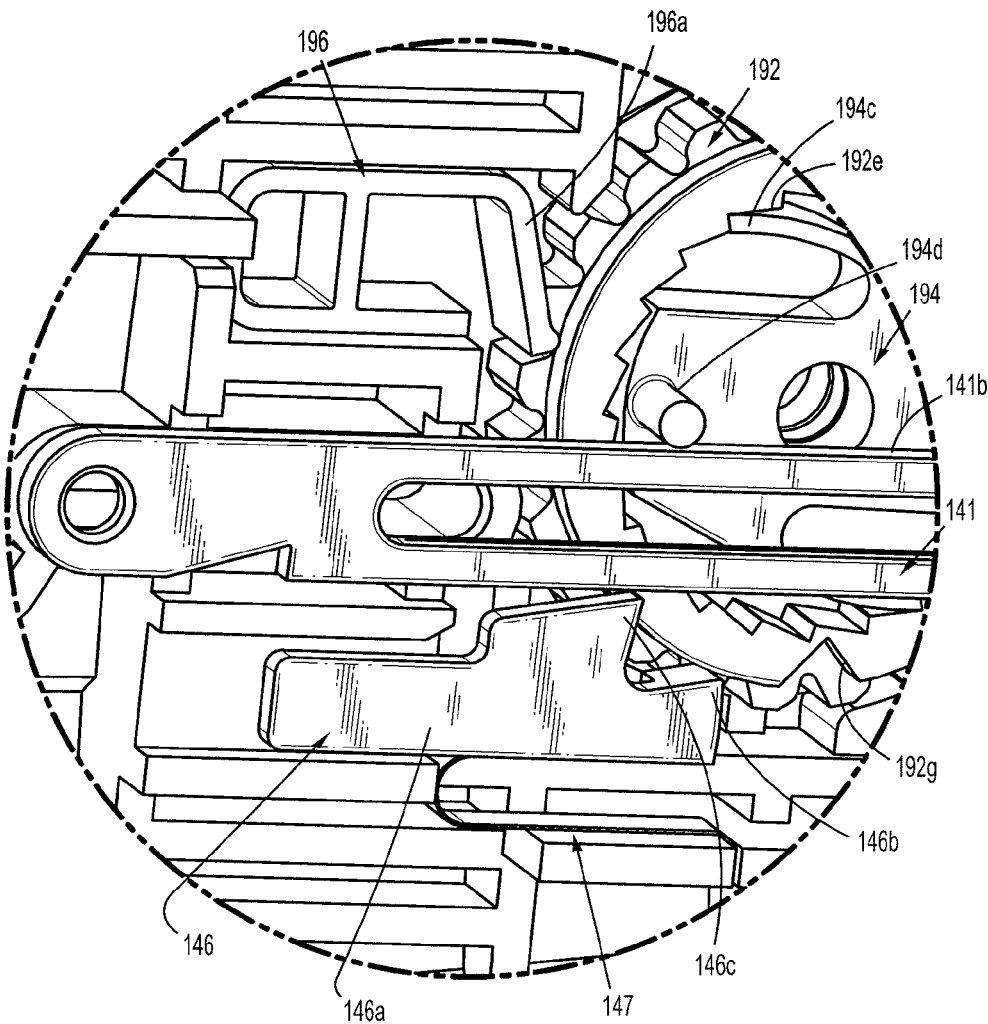
FIG. 8 is an enlarged view of the indicated area of detail of FIG. 7.
Figure 9:
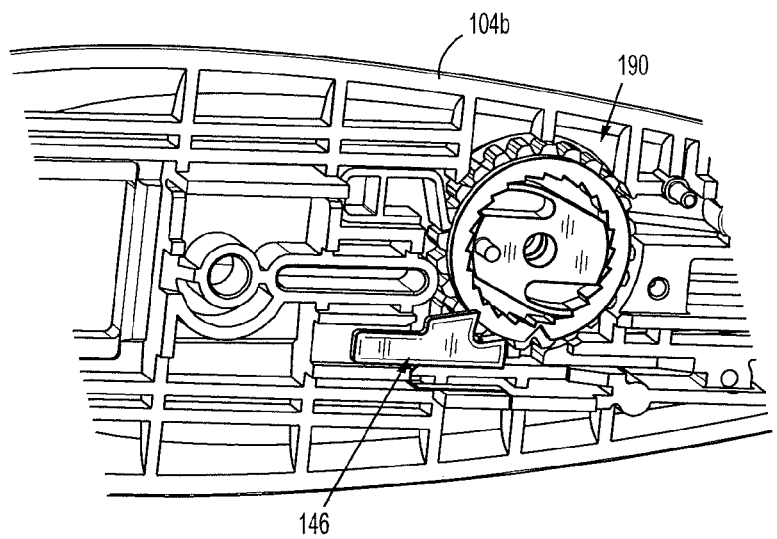
FIG. 9 is a perspective view of a handle assembly with a housing half-section, the drive channel, and the ratchet removed therefrom.
Figure 10:
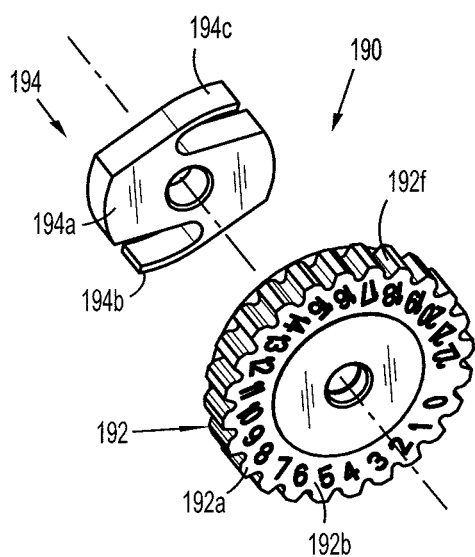
FIG. 10 is a front, perspective view, with parts separated, of a counter and a clutch of the mechanical counter assembly.
Figure 11:
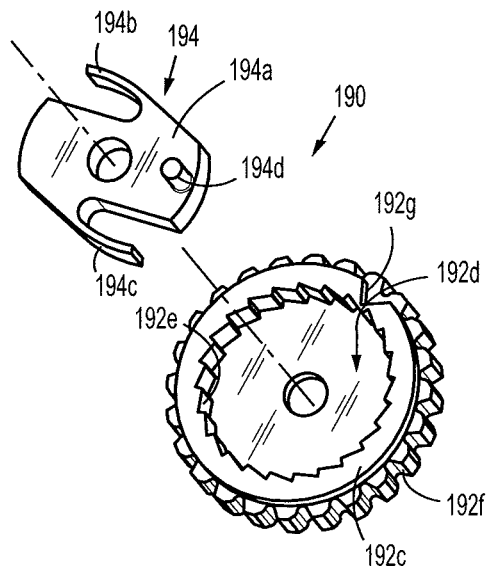
FIG. 11 is a rear, perspective view, with parts separated, of the counter and the clutch of the mechanical counter assembly of FIG. 10.
Figure 12:
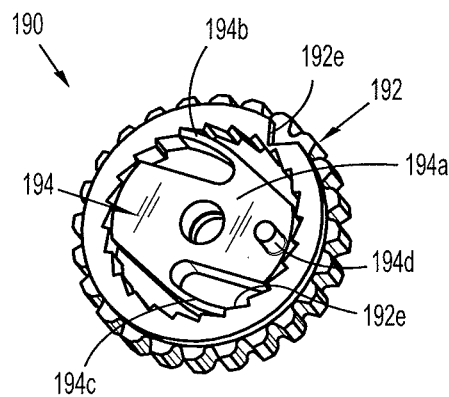
FIG. 12 is a rear, perspective view of the counter and the clutch of the mechanical counter assembly of FIGS. 10 and 11.
Figure 13:
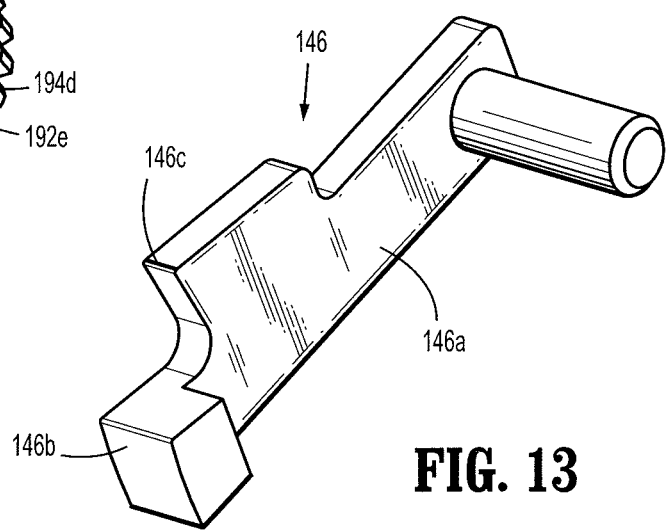
FIG. 13 is a perspective view of a lock-out of the clip applier of FIGS. 1-4.

As seen in FIGS. 5 and 6, drive channel 140 defines an angled slot 140a formed therein at a location so as to slidably receive clutch pin 194d extending from body portion 194a of counter clutch 194. Angled slot 140a of drive channel 140 extends in a direction away from a longitudinal axis of clip applier 100 from a proximal to a distal direction.

As seen in FIGS. 4, 5, 7 and 8, clip applier 100 includes a ratchet rack member 141 slidably disposed in lower housing half 104b. Rack member 141 is pinned to drive pin 124 such that translation of drive pin 124 relative to housing 104 results in concomitant translation of rack member 141. Rack member 141 is disposed in housing 104 such that clutch pin 194d of counter clutch 194 rides along or contacts a side edge 141b thereof. Rack member 141 includes ratchet teeth 141a formed along an edge thereof and are configured and adapted to engage with a ratchet pawl 142 supported in housing 104. Rack member 141 and pawl 142 define a ratchet mechanism 144.

In use, as drive channel 140 is moved axially by drive pin 124, rack member 141 is also moved. Rack teeth 141a of rack member 141 has a length which allows pawl 142 to reverse and advance back over rack member 141 when rack member 141 changes between proximal and distal movement as drive channel 140 reaches a proximal-most or distal-most position.

Pawl 142 is pivotally connected to lower housing half 104b by a pawl pin at a location wherein pawl 142 is in substantial operative engagement with rack member 141. Pawl 142 is engageable with rack member 141 to restrict longitudinal movement of rack member 141 and, in turn, drive channel 140. Ratchet mechanism 144 further includes a pawl spring 145 configured and positioned to bias pawl 142 into operative association with rack member 141. Pawl spring 145 functions to maintain the teeth of pawl 142 in engagement with the teeth 141a of rack member 141, as well as to maintain pawl 142 in a rotated or canted position.

As seen in FIGS. 4, 5, 7-9 and 13, clip applier 100 further includes a lock out 146 pivotally connected or supported in housing 104. Lock out 146 includes a body portion 146a, a first catch 146b formed at one and of body portion 146a, and a second catch 146c extending from a side edge of body portion 146a. First catch 146b is configured and dimensioned to engage groove 192g formed in the outer periphery of the inner rim of counter dial 192. Second catch 146c is configured and dimensioned to engage a notch 141c formed in a side edge of rack member 141. A biasing member 147 is provided to maintain first catch 146b of lock out 146 in contact with the outer periphery of the inner rim of counter dial 192.

Figures 14, 14A:
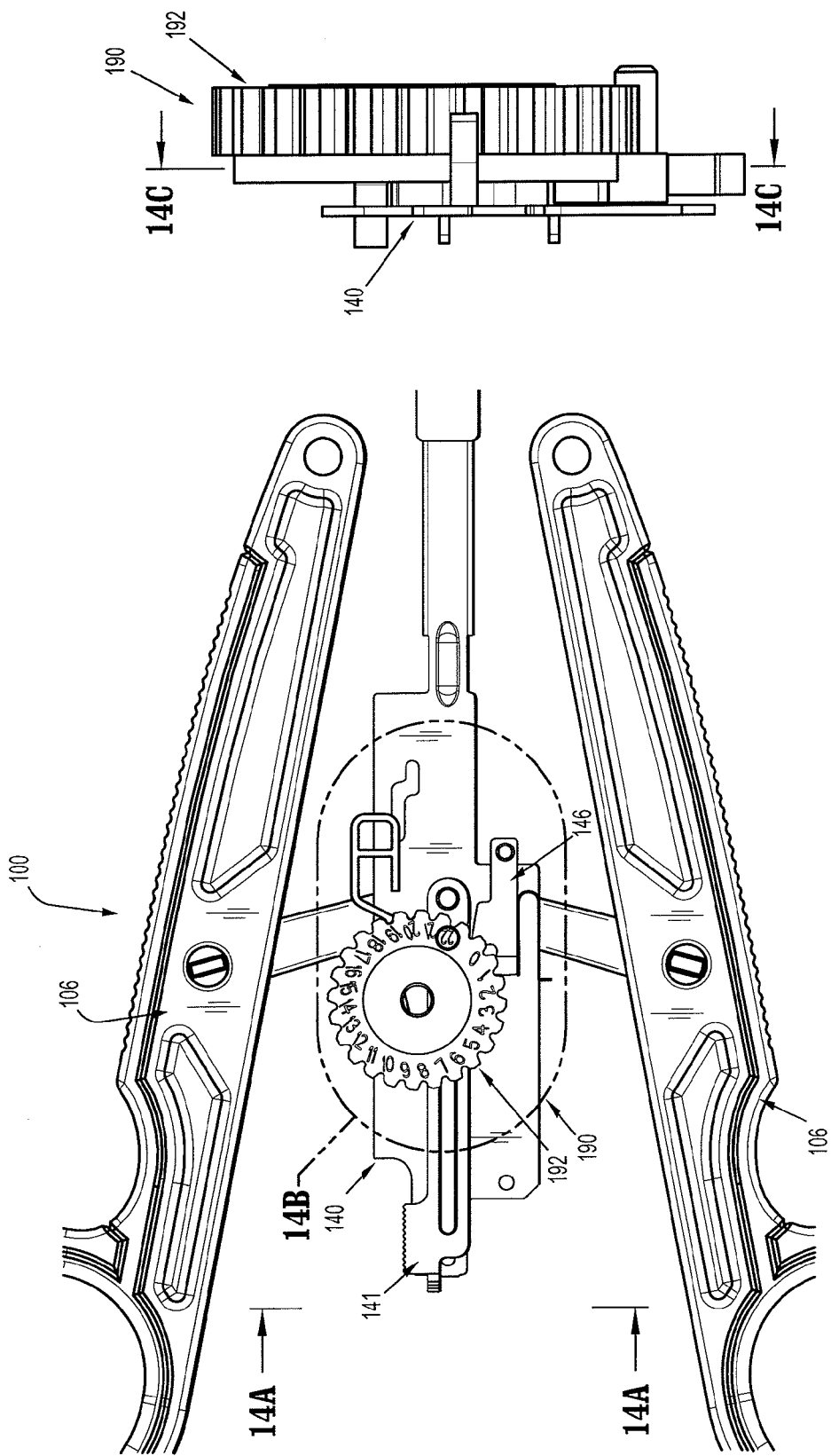
FIG. 14 is a top plan, schematic illustration of the mechanical counter assembly operatively connected to the drive channel when the clip applier is in an original unactuated position.
FIG. 14A is a side view of the mechanical counter assembly as viewed along 14A-14A of FIG. 14.
Figure 14B:
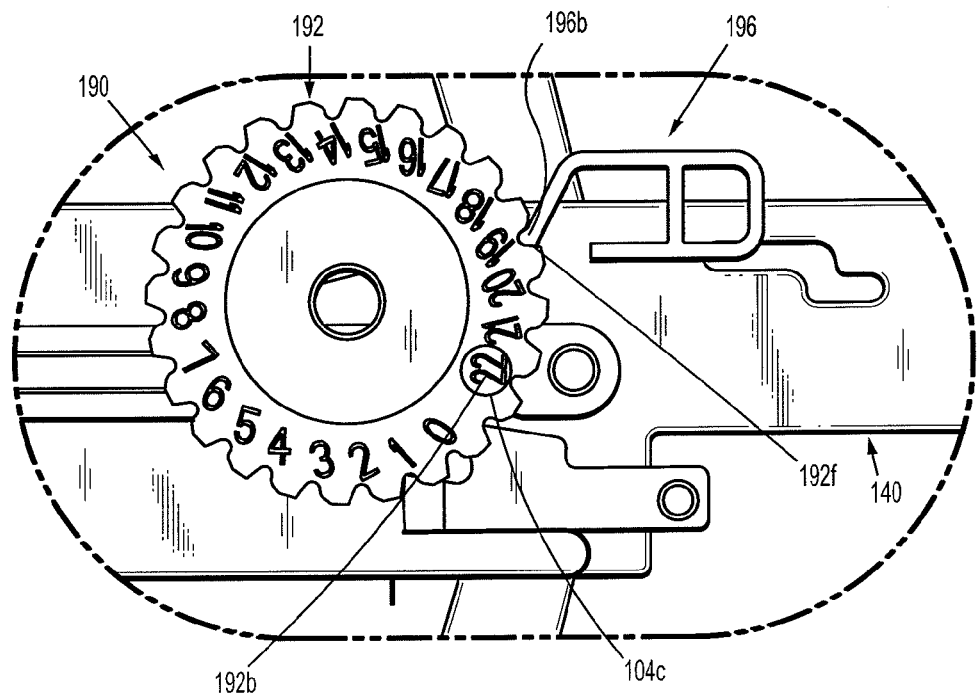
FIG. 14B is an enlarged view of the indicated area of detail of FIG. 14.
Figure 14C:
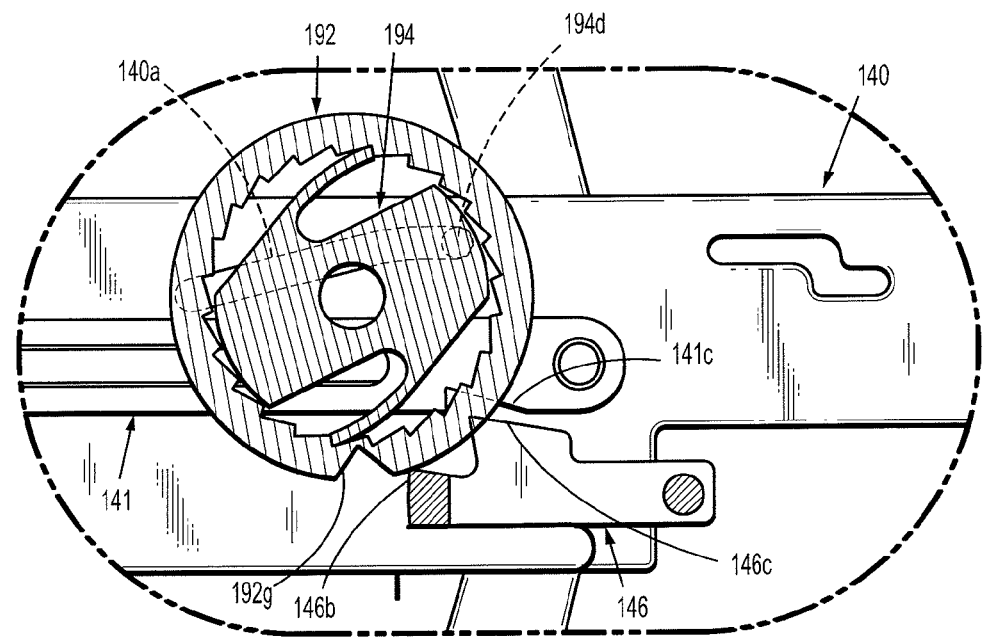
FIG. 14C is a cross-sectional view of the mechanical counter assembly as taken along 14C-14C of FIG. 14A.

Turning now to FIGS. 14-19B, the operation of clip applier 100 is provided. Prior to any initial squeezing of handles 106 of clip applier 100 and with clip applier 100 fully loaded with clips "C," as seen in FIGS. 14-14C, drive channel 140 is located at a proximal-most position, indicia 192b of counter dial 192 of mechanical counter mechanism 190, relating to a fully loaded clip applier 100, in the present instance being fully loaded with twenty-two (22) clips, is visible through window 104c formed in housing half 104b. Accordingly, as seen in FIG. 14B, the numeral "22" is visible through window 104c. Also, as seen in FIG. 14B, resilient finger 196a of latch member 196 is engaged in a groove 192f formed around the outer periphery of counter dial 192.

As seen in FIG. 14C, prior to any squeezing of handles 106, clutch pin 194d of counter clutch 194 is disposed at a distal end of angled slot 140a of drive channel 140. Also, first catch 146b of lock out 146 is in contact with the outer periphery of the inner rim of counter dial 192 so that second catch 146c of lock out 146 is disengaged from rack member 141. Moreover, prior to any squeezing of handles 106, and when clip applier 100 is fully loaded with clips, groove 192g formed in the outer periphery of the inner rim of counter dial 192 is oriented distal of first catch 146b of lock out 146.

Figure 15:
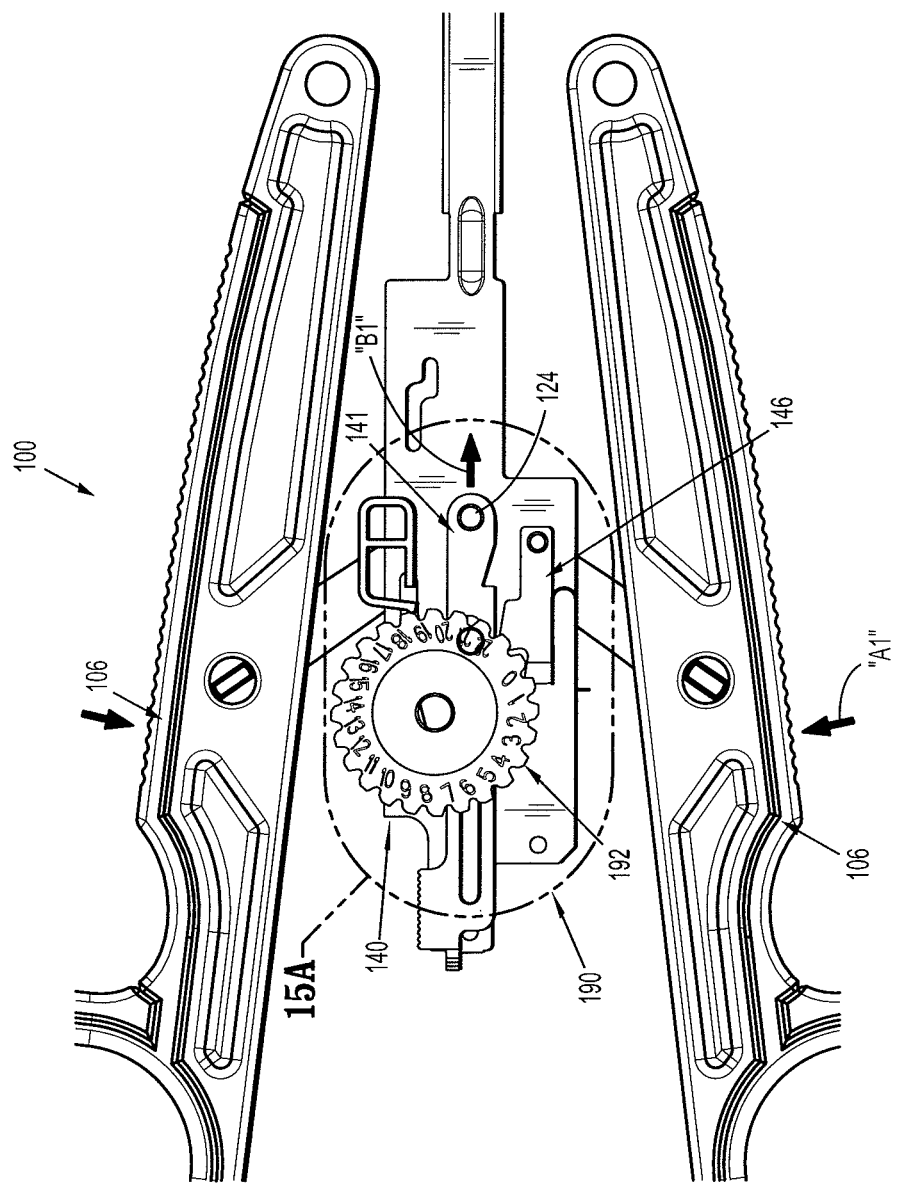
FIG. 15 is a top plan, schematic illustration of the mechanical counter assembly operatively connected to the drive channel when the clip applier is initially actuated.
Figure 15A:
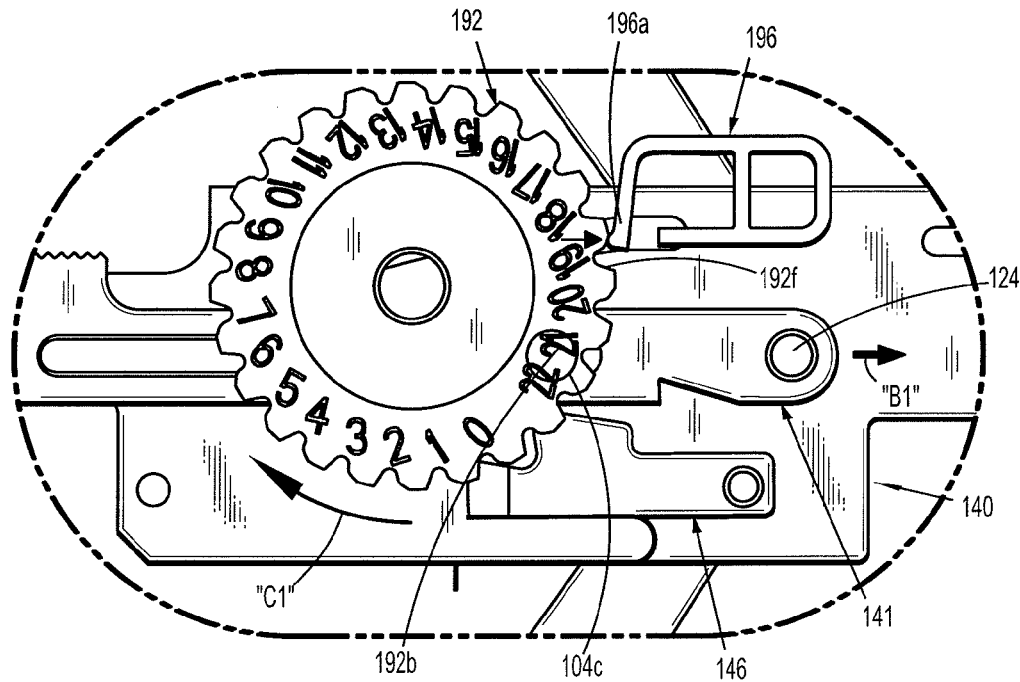
FIG. 15A is an enlarged view of the indicated area of detail of FIG. 15.
Figure 15B:
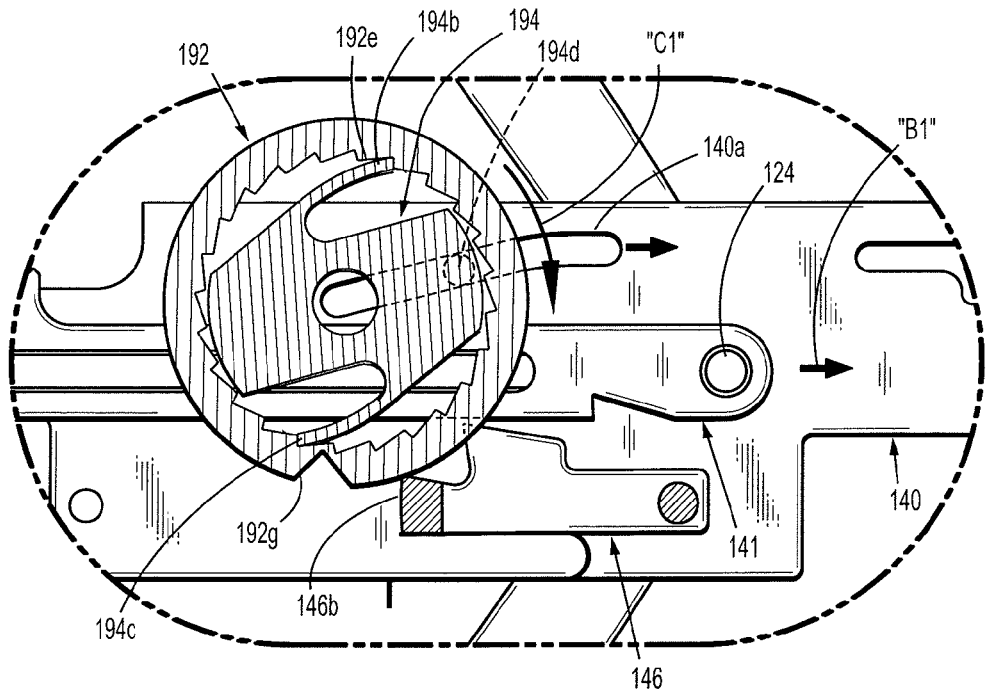
FIG. 15B is a cross-sectional view of the mechanical counter assembly as taken along 14C-14C of FIG. 14A, during the initial actuation of the clip applier.

As seen in FIGS. 15-15B, during an initial squeeze of handles 106, as indicated by arrow "A1," drive pin 124 translates drive channel 140 and rack member 141 in a distal direction, as indicated by arrow "B1." As drive channel 140 is translated in a distal direction, angled slot 140a of drive channel 140 is moved in a distal direction relative to clutch pin 194d of counter clutch 194, clutch pin 194d is cammed through angled slot 140a of drive channel 140 causing counter clutch 194 to rotate in the direction of arrow "C1." As counter clutch 194 is rotated in the direction of arrow "C1," as seen in FIG. 15B, resilient fingers 194b, 194c thereof engage uni-directional teeth 192e of dial 192, thereby causing dial 192 to also rotate in the direction of arrow "C1." Moreover, as dial 192 is rotated in the direction of arrow "C1," groove 192g formed in the outer periphery of the inner rim of counter dial 192 is rotated away from first catch 146b of lock out 146 as first catch 146b continues to ride along the outer periphery of the inner rim of counter dial 192.

As dial 192 is rotated in the direction of arrow "C1," as seen in FIG. 15A, indicia 192b of numeral "22" is moved relative to window 104c formed in housing half 104b, thereby beginning to decrement. Additionally, as dial 192 is rotated in the direction of arrow "C1," resilient finger 196a of latch member 196 begins to disengage the groove 192f formed around the outer periphery of counter dial 192.

Figure 16:
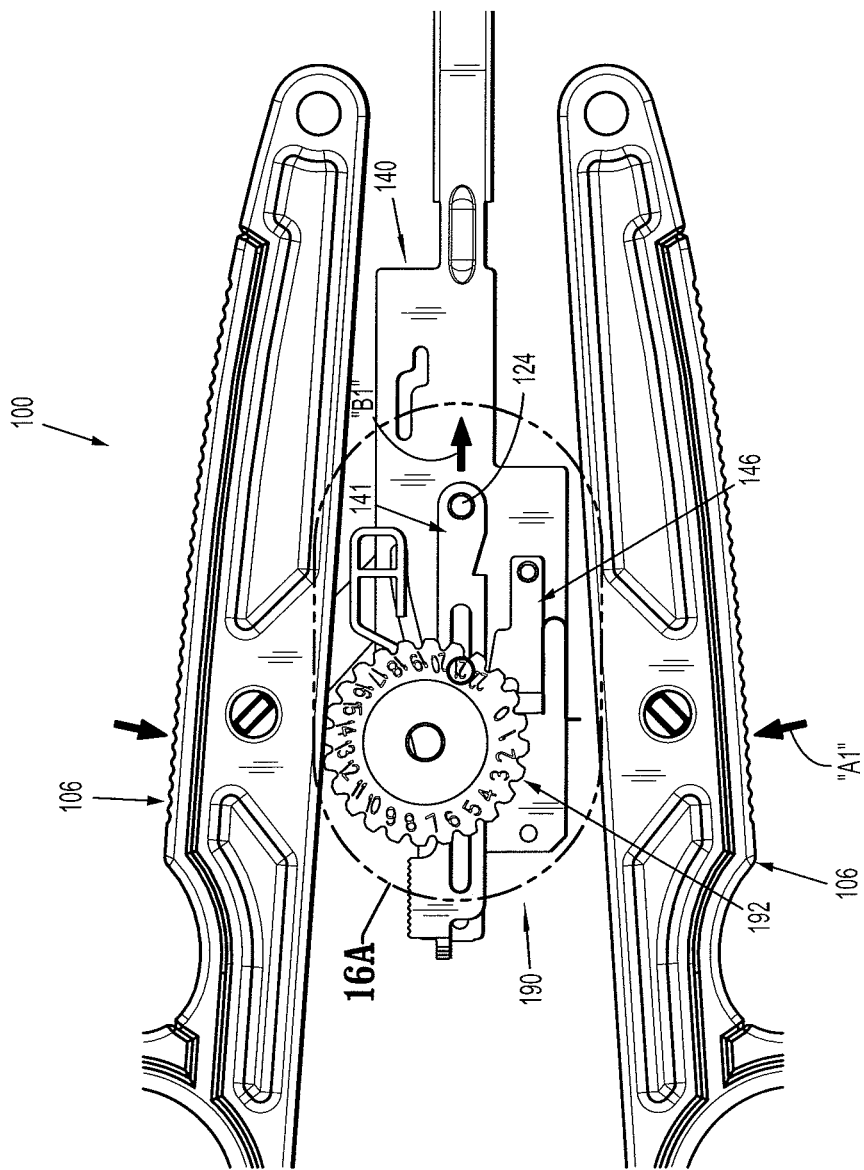
FIG. 16 is a top plan, schematic illustration of the mechanical counter assembly operatively connected to the drive channel when the clip applier is fully actuated.
Figure 16A:
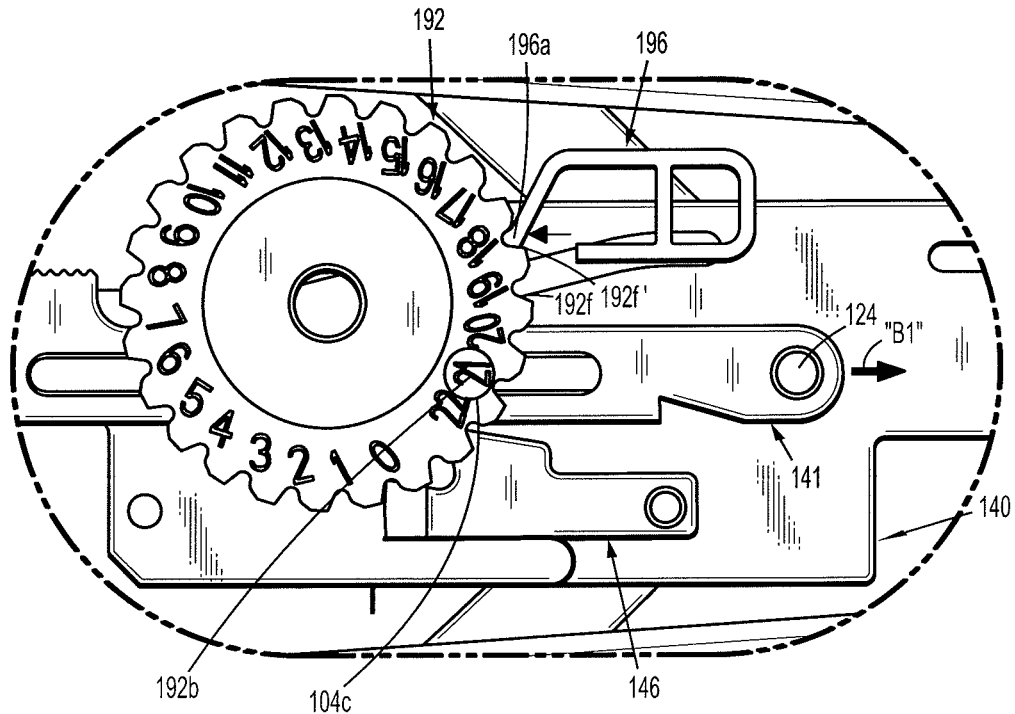
FIG. 16A is an enlarged view of the indicated area of detail of FIG. 16.
Figure 16B:
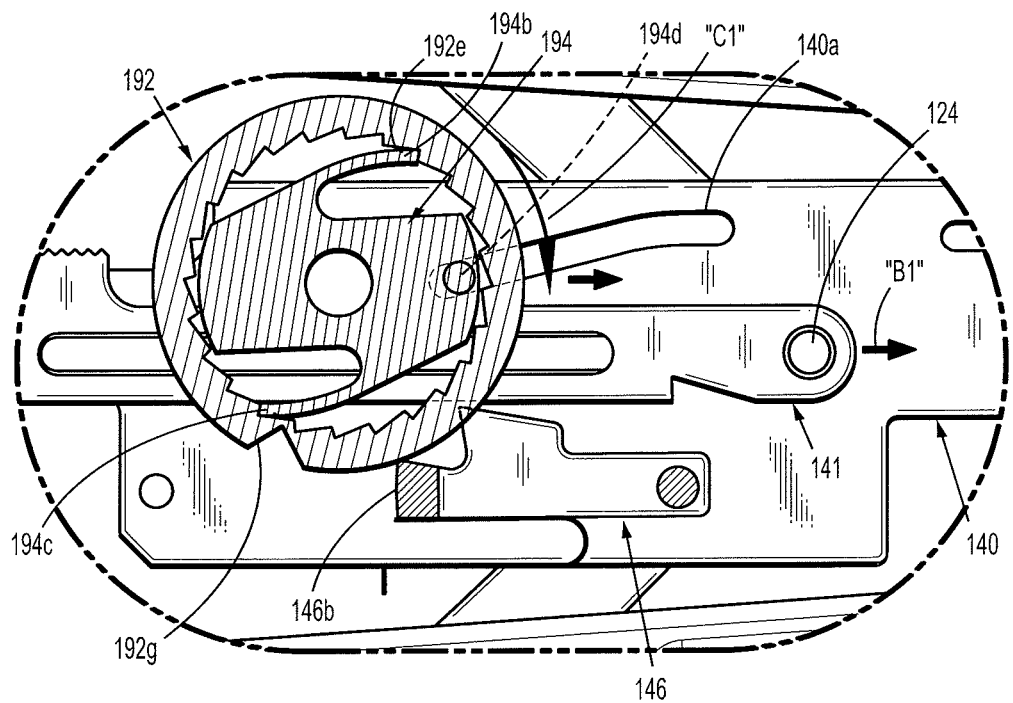
FIG. 16B is a cross-sectional view of the mechanical counter assembly as taken along 14C-14C of FIG. 14A, following the full actuation of the clip applier.

As seen in FIGS. 16-16B, during a final or complete squeeze of handles 106, as indicated by arrow "A1," drive pin 124 further translates drive channel 140 and rack member 141 in a distal direction, as indicated by arrow "B1." As drive channel 140 is further translated in a distal direction, angled slot 140a of drive channel 140 is further moved in a distal direction relative to clutch pin 194d of counter clutch 194, clutch pin 194d is further cammed through angled slot 140a of drive channel 140 causing counter clutch 194 to further rotate in the direction of arrow "C1." As counter clutch 194 is further rotated in the direction of arrow "C1," as seen in FIG. 16B, resilient fingers 194b, 194c continue to cause dial 192 to rotate in the direction of arrow "C1." Moreover, as dial 192 is further rotated in the direction of arrow "C1," groove 192g formed in the outer periphery of the inner rim of counter dial 192 is further rotated away from first catch 146b of lock out 146 as first catch 146b further continues to ride along the outer periphery of the inner rim of counter dial 192.

As dial 192 is further rotated in the direction of arrow "C1," as seen in FIG. 16A, indicia 192b of numeral "22" is completely moved out of view of window 104c formed in housing half 104b and new numeral "21" is moved into view of window 104c, thereby fully being decremented. This change of numeral, or decrementing, coinciding with a formation and/or firing/ejection/release of a clip from clip applier 100. In this manner, the user is shown the number of clips remaining in clip applier 100 and available to fire. Additionally, as dial 192 is further rotated in the direction of arrow "C1," resilient finger 196a of latch member 196 moves into engagement in a groove 192f adjacent to groove 192f formed around the outer periphery of counter dial 192.

Figure 17:
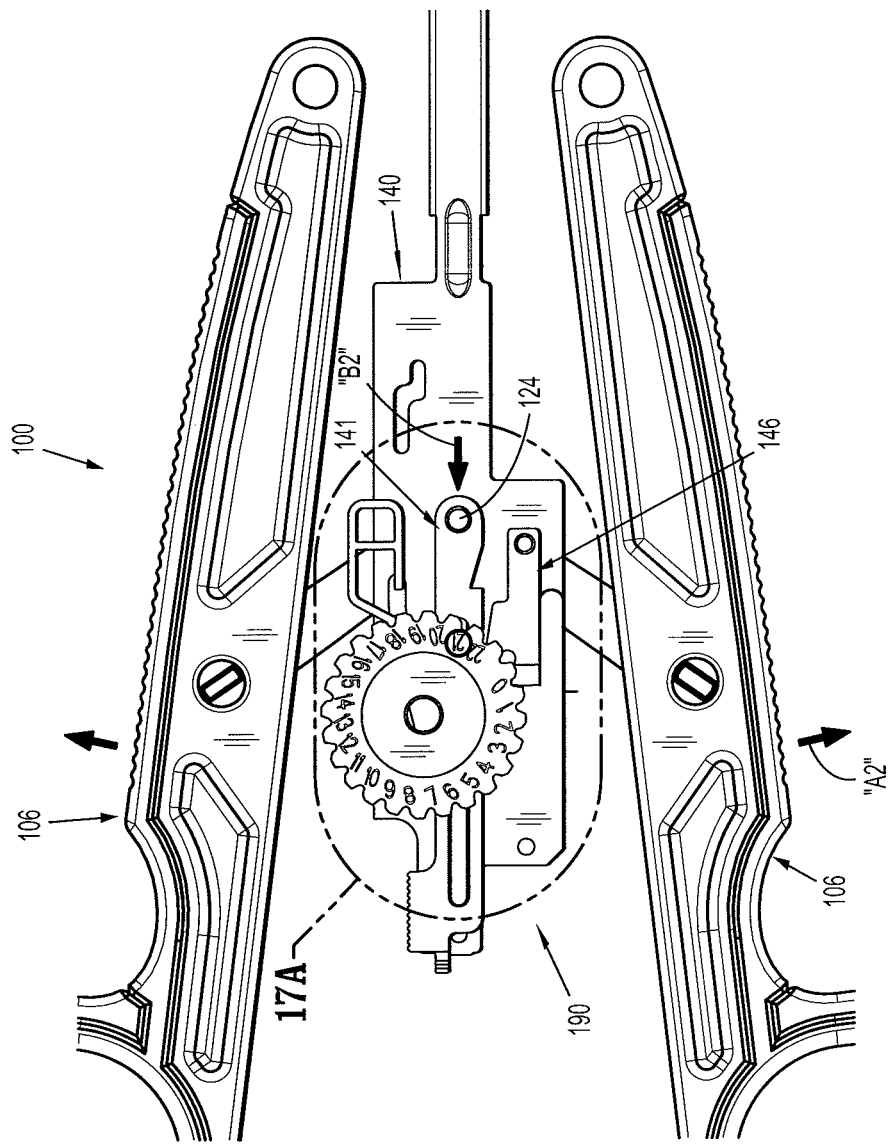
FIG. 17 is a top plan, schematic illustration of the mechanical counter assembly operatively connected to the drive channel when the clip applier is released after full actuation.
Figure 17A:
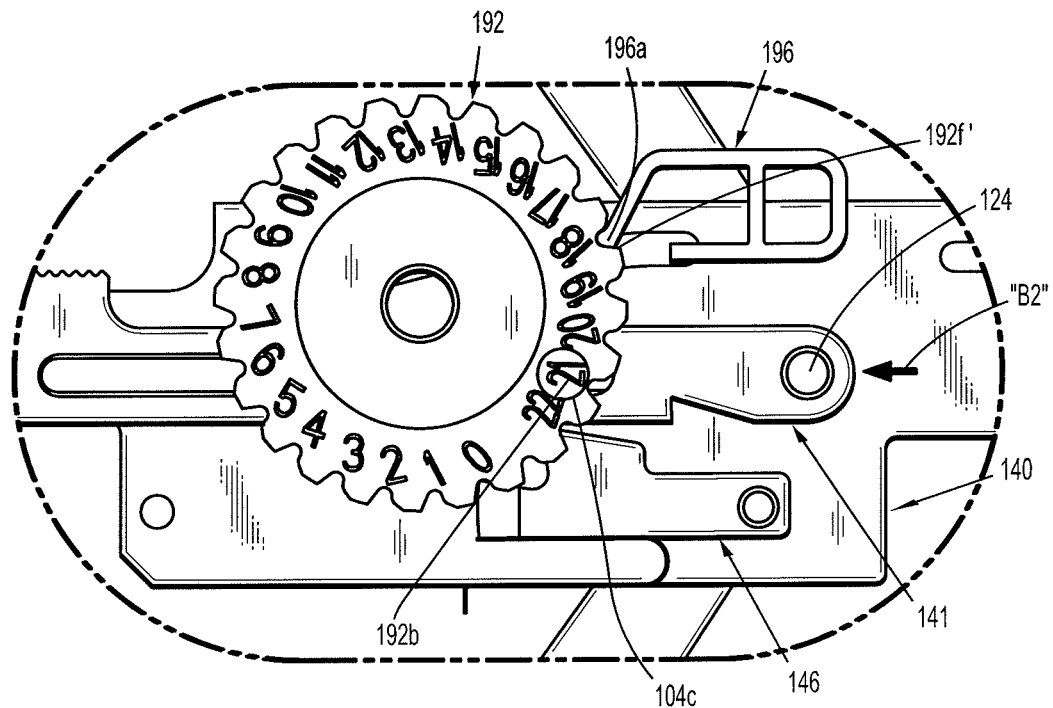
FIG. 17A is an enlarged view of the indicated area of detail of FIG. 17.
Figure 17B:
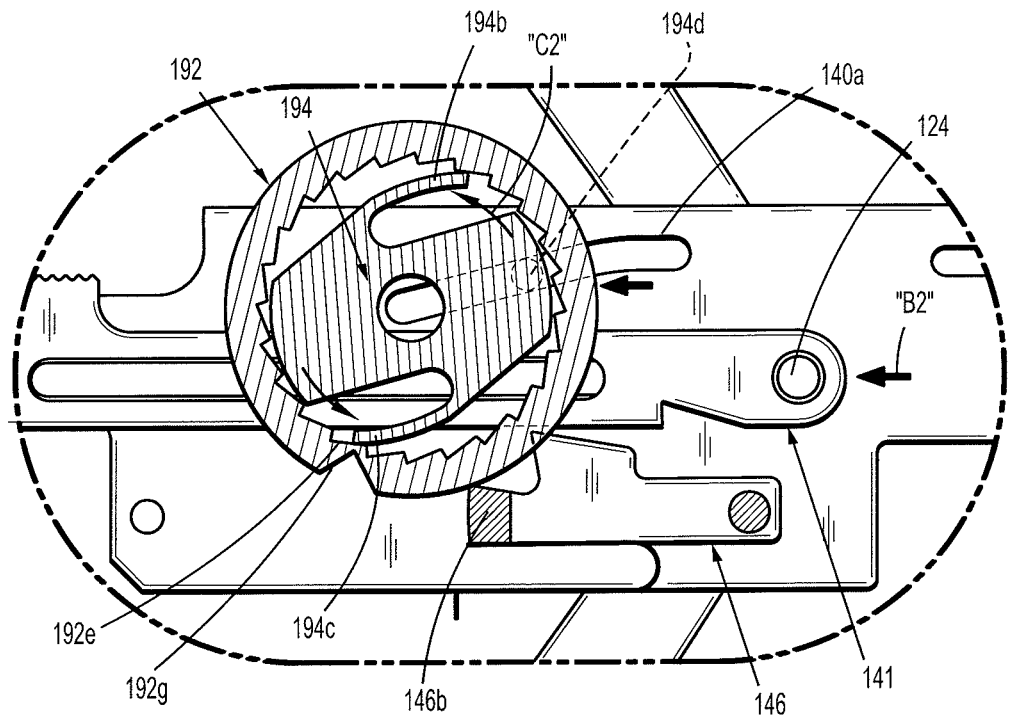
FIG. 17B is a cross-sectional view of the mechanical counter assembly as taken along 14C-14C of FIG. 14A, during a release of the clip applier following full actuation.
Figure 18:
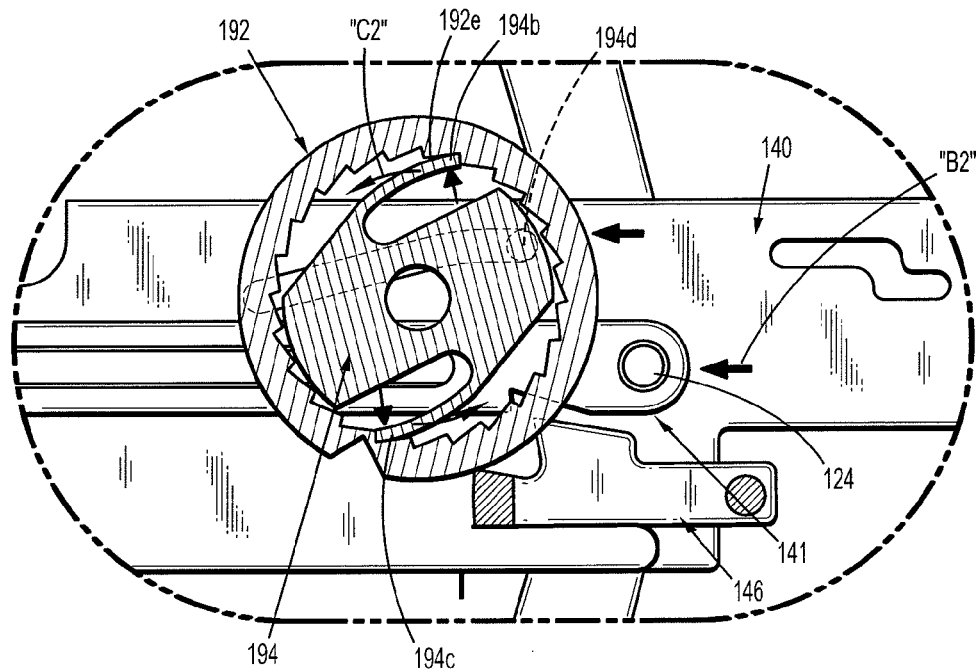
FIG. 18 is a cross-sectional view of the mechanical counter assembly as taken along 14C-14C of FIG. 14A, illustrating the mechanical counter assembly fully re-set.

Turning now to FIGS. 17-18, during an opening of handles 106, as indicated by arrow "A2," drive pin 124 translates drive channel 140 and rack member 141 in a proximal direction, as indicated by arrow "B2." As drive channel 140 is translated in a proximal direction, angled slot 140a of drive channel 140 is moved in a proximal direction relative to clutch pin 194d of counter clutch 194, clutch pin 194d is cammed through angled slot 140a of drive channel 140 causing counter clutch 194 to rotate in the direction of arrow "C2," opposite to "C1." As counter clutch 194 is rotated in the direction of arrow "C2," as seen in FIG. 17B, resilient fingers 194b, 194c are caused to deflect and snap over uni-directional teeth 192e of dial 192. as seen from FIG. 17A, any frictional forces tending to cause dial 192 to also rotate in the direction of arrow "C2" and negated by the engagement of resilient finger 196a of latch member 196 in groove 192f formed around the outer periphery of counter dial 192, thereby maintaining the rotational orientation of dial 192.

With dial 192 being held or maintained in this rotational orientation, indicia 192b of numeral "21" is maintained in view in window 104c.

As seen in FIG. 18, when drive channel 140 has been moved back to the fully proximal position, resilient fingers 194b, 194c of counter clutch 194 are re-set in engagement with adjacent uni-directional teeth 192e of dial 192.

Additionally, as dial 192 is further rotated in the direction of arrow "C1," resilient finger 196a of latch member 196 moves into engagement in a groove 192f adjacent to groove 192f formed around the outer periphery of counter dial 192.

Figure 19:
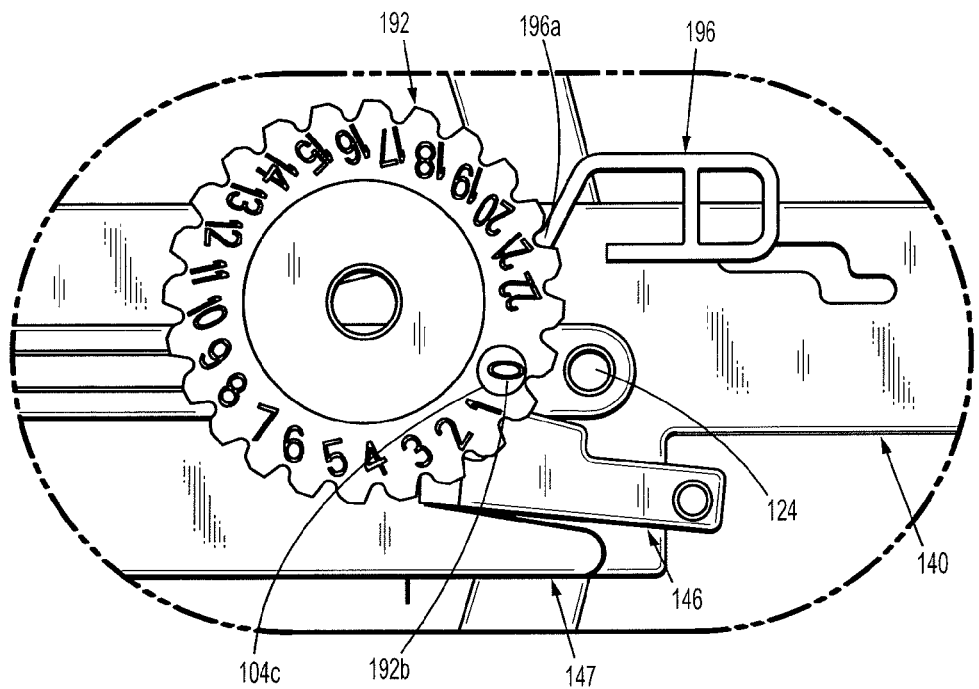
FIG. 19 is a top, plan view of the mechanical counter assembly, illustrating the counter at a "zero" position and locked out.
Figure 19A:
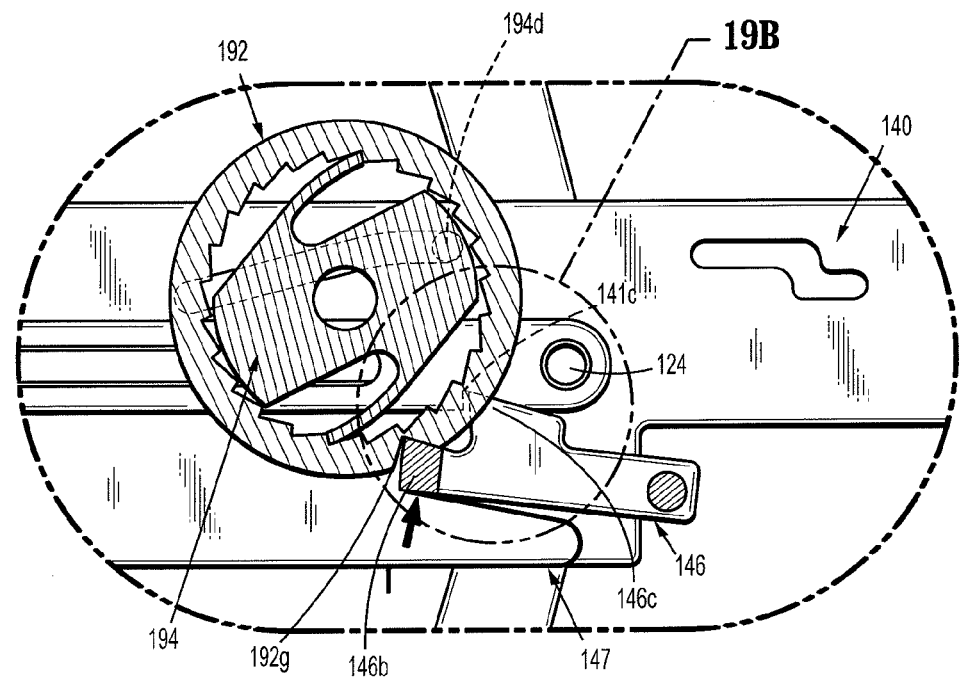
FIG. 19A is a cross-sectional view of the mechanical counter assembly as taken along 14C-14C of FIG. 14A, illustrating the counter at a "zero" position and locked out.
Figure 19B:
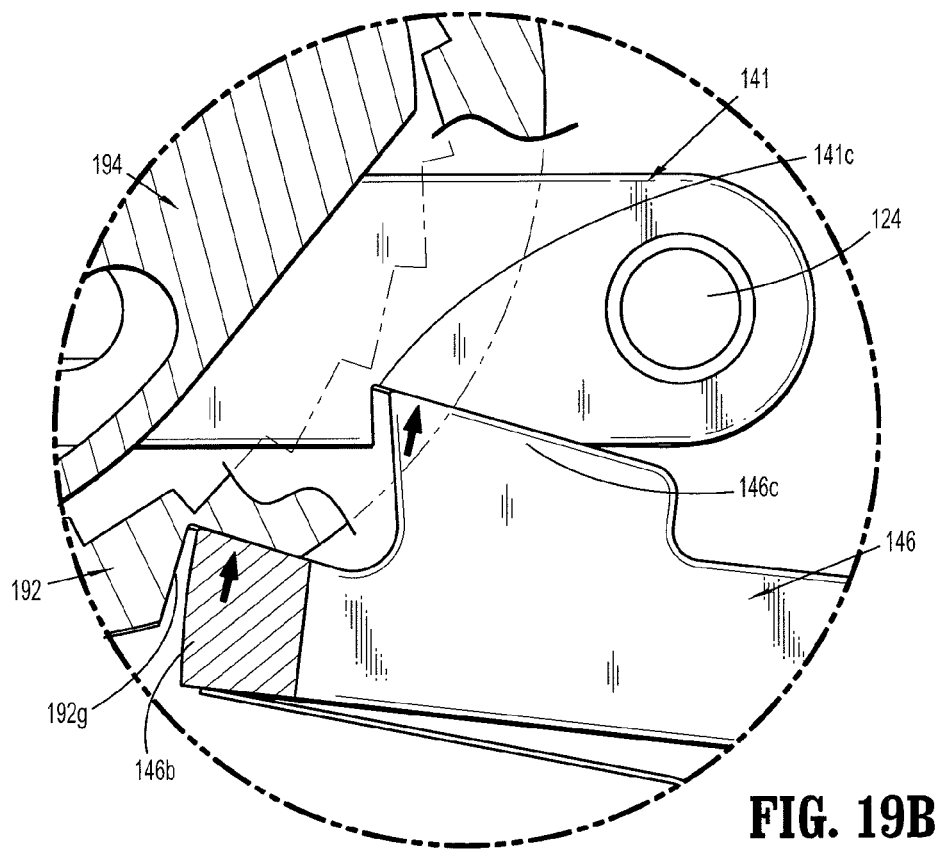
FIG. 19B is an enlarged view of the indicated area of detail of FIG. 19A.

Turning now to FIGS. 19-19B, during the squeezing of handles 106, upon the firing of a final clip loaded in clip applier 100, indicia 192b of dial in the form of numeral "0" is completely moved into view of window 104c formed in housing half 104b, thereby indicating to the user that no more clip are present in clip applier 100. When dial 192 has been rotated to this position, as seen in FIGS. 19A and 19B, groove 192g formed in the outer periphery of the inner rim of counter dial 192 is rotated into registration with first catch 146b of lock out 146. In this position, biasing member 147, acting on lock out 146, urges first catch 146b of lock out 146 into groove 192g of dial 192.

Additionally, in the present position, second catch 146c of lock out 146 is moved into notch 141c formed in side edge of rack member 141 and thus into the path of proximal translation of rack member 141. Accordingly, as handles 106 are released and drive pin 124 begins to move rack member 141 in a proximal direction, notch 141c of rack member 141 engages second catch 146c of lock out 146 thereby prohibiting rack member 141 from returning to a proximal most or home position. With rack member 141 being inhibited or blocked from returning to the proximal most position, ratchet pawl 142 of ratchet mechanism 144 (see FIG. 5) is prevented from resetting itself. Since pawl 142 is prevented from resetting itself, handles 106 can not be re-actuated or re-squeezed since they have only been partially opened. Once again, reference may be made to U.S. Provisional Application No. 61/091,467, filed on Aug. 25, 2008, entitled "Surgical Clip Applier;" U.S. Provisional Application No. 61/091,485, filed on Aug. 25, 2008, entitled "Surgical Clip Applier and Method of Assembly;" and U.S. Provisional Application No. 61/286,569, filed on Dec. 15, 2009, entitled "Surgical Clip Applier", for a detailed discussion of the structure, operation, and method of assembly of various components of surgical clip applier 100.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
a housing;
at least one handle pivotably connected to the housing;
a channel assembly extending distally from the housing;
a plurality of clips loaded in a clip carrier;
a drive channel translatably supported in the housing and the channel assembly, the drive channel being translated upon actuation of the at least one handle; and
a counter mechanism supported in the housing and including:
a counter dial rotatably supported in the housing;
a counter clutch operatively connected to the drive channel, the counter clutch concentrically and rotatably nested in a bore defined in the counter dial such that rotation of the counter clutch in a first direction results in rotation of the counter dial in the first direction, and rotation of the counter clutch in a second direction results in no rotation of the counter dial, wherein translation of the drive channel in a first direction relative to the counter mechanism directly causes the counter clutch to rotate in the first direction, and translation of the drive channel in a second direction relative to the counter mechanism directly causes the counter clutch to rotate in the second direction;
indicia disposed on the counter dial and visible through the housing, wherein the indicia corresponds to a quantity of clips loaded in the clip applier, wherein the indicia decrements upon each firing of the clip applier resulting in a reduction in the quantity of clips remaining of the plurality of clips.

2. The clip applier according to claim 1, wherein the counter clutch includes a uni-directional clutch member configured to rotate the counter dial in a single direction.

3. The clip applier according to claim 1, wherein the counter mechanism includes a latch member operatively engaged with the counter dial, wherein the latch member permits rotation of the counter dial in the first direction and inhibits rotation of the counter mechanism in a direction opposite to the first direction.

4. The clip applier according to claim 3, wherein the counter dial includes a plurality of grooves formed in an outer periphery thereof, and the latch member includes a resilient finger biased into engagement with the plurality of grooves of the counter dial.

5. The clip applier according to claim 1, wherein the counter clutch includes at least one resilient finger extending therefrom for engagement with uni-directional teeth formed in a perimetrical surface of the bore of the counter dial.

6. The clip applier according to claim 5, wherein the drive channel defines an angled slot therein, and wherein the counter clutch includes a clutch pin extending from a surface thereof and slidably disposed in the angled slot of the drive channel, wherein translation of the drive channel in the first direction relative to the counter mechanism causes the clutch pin to be cammed by the angled slot thereof thereby causing the counter clutch to rotate in the first direction, and translation of the drive channel in the second direction relative to the counter mechanism causes the clutch pin to be cammed by the angled slot thereof thereby causing the counter clutch to rotate in the second direction.

7. The clip applier according to claim 6, wherein the counter mechanism includes a latch member operatively engaged with the counter dial, wherein the latch member permits rotation of the counter dial in the first direction and inhibits rotation of the counter mechanism in a direction opposite to the first direction.

8. The clip applier according to claim 7, wherein the counter dial includes a plurality of grooves formed in an outer periphery thereof, and the latch member includes a resilient finger biased into engagement with the plurality of grooves of the counter dial.

9. The clip applier according to claim 1, wherein the counter mechanism includes:
a lock out groove formed in an outer perimetrical edge of the counter dial; and
a lock out supported in the housing and biased such that a first catch thereof engages against the outer perimetrical edge of the counter dial,
wherein as the counter dial is rotated in the first direction and the lock out groove of the counter dial is brought into registration with the first catch of the lock out, the first catch of the lock out moves into and engages the lock out groove to inhibit further rotation of the counter dial in the first direction.

10. The clip applier according to claim 9, wherein the lock out includes a second catch, and wherein the second catch moves into a path of a translating member of the clip applier when the first catch of the lock out is moved into the lock out groove of the counter dial, thereby inhibiting a translation of the translating member of the clip applier.

11. The clip applier according to claim 10, wherein the lock out groove of the counter dial moves into registration with the first catch of the lock out when a final clip of the plurality of clips has been fired.

12. The clip applier according to claim 11, wherein the lock out groove of the counter dial is associated with the indicia on the counter mechanism indicating that the final clip has been fired.

13. The clip applier according to claim 12, wherein the indicia on the counter mechanism indicating that the final clip of the plurality of clip has been fired is represented by a number "zero".

14. The clip applier according to claim 10, further comprising a ratchet mechanism including:
a ratchet pawl pivotably supported in the housing; and
a rack member provided on the translating member, wherein the rack member is in operative registration with the ratchet pawl, and wherein the rack member translates across the ratchet pawl as the translating member translates.

15. The clip applier according to claim 14, wherein the ratchet mechanism is prevented from re-setting when the rack member has not completed a full translation.

16. A surgical clip applier, comprising:
a housing;
at least one handle pivotably connected to the housing;
a channel assembly extending distally from the housing;
a plurality of clips loaded in a clip carrier;
a drive channel translatably supported in the housing and the channel assembly, the drive channel being translated upon actuation of the at least one handle; and
a counter mechanism supported in the housing, the counter mechanism including indicia visible through the housing, wherein the indicia corresponds to a quantity of clips loaded in the clip applier, wherein the indicia decrements upon each firing of the clip applier resulting in a reduction in the quantity of clips remaining of the plurality of clips, the counter mechanism including a counter clutch concentrically and rotatably nested in a bore defined in the counter mechanism, the counter clutch being operatively connected to the drive channel wherein translation of the drive channel in a first direction relative to the counter mechanism directly causes the counter clutch to pivot in a first direction, and translation of the drive channel in a second direction relative to the counter mechanism directly causes the counter clutch to pivot in a second direction.

17. The clip applier according to claim 16, wherein the counter mechanism is rotatably supported in the housing and the counter clutch is configured to rotate the counter mechanism in a single direction to decrement the indicia upon a pivot thereof.

18. The clip applier according to claim 16, wherein the counter mechanism includes a counter dial rotatably supported in the housing and including the indicia thereon, the counter clutch being nested concentrically within the counter dial and the counter mechanism.

19. The clip applier according to claim 18, wherein pivoting the counter clutch in the first direction results in rotation of the counter dial in the first direction, and pivoting the counter clutch in the second direction results in no rotation of the counter dial.

\* \* \* \* \*